(12) United States Patent
Venkatesh et al.

(10) Patent No.: US 9,572,781 B2
(45) Date of Patent: Feb. 21, 2017

(54) ORALLY DISINTEGRATING TABLET COMPOSITIONS COMPRISING COMBINATIONS OF NON-OPIOID AND OPIOID ANALGESICS

(75) Inventors: Gopi Venkatesh, Vandalia, OH (US); Michael Gosselin, Springboro, OH (US); James Clevenger, Vandalia, OH (US); Jin-Wang Lai, Springboro, OH (US)

(73) Assignee: Adare Pharmaceuticals, Inc., Lawrenceville, NJ (US)

( * ) Notice: Subject to any disclaimer, the term of this patent is extended or adjusted under 35 U.S.C. 154(b) by 291 days.

(21) Appl. No.: 12/772,776

(22) Filed: May 3, 2010

(65) Prior Publication Data

US 2011/0003006 A1  Jan. 6, 2011

Related U.S. Application Data

(60) Provisional application No. 61/174,780, filed on May 1, 2009, provisional application No. 61/174,788, filed on May 1, 2009.

(51) Int. Cl.
*A61K 9/16* (2006.01)
*A61K 9/50* (2006.01)

(52) U.S. Cl.
CPC .......... *A61K 9/5047* (2013.01); *A61K 9/5078* (2013.01)
USPC ......................................... 424/495

(58) Field of Classification Search
None
See application file for complete search history.

(56) References Cited

U.S. PATENT DOCUMENTS

| 4,891,223 A | 1/1990 | Ambegaonkar et al. |
| 5,185,352 A | 2/1993 | Aranda et al. |
| 6,210,714 B1 * | 4/2001 | Oshlack et al. ............... 424/476 |
| 6,485,747 B1 | 11/2002 | Flanagan et al. |
| 2004/0091458 A1 | 5/2004 | Morris et al. |

(Continued)

FOREIGN PATENT DOCUMENTS

| RU | 2232600 C2 | 7/2004 |
| WO | WO 90/01477 A1 | 2/1990 |

(Continued)

OTHER PUBLICATIONS

Evonik brochure [downloaded on Jul. 17, 2014 from the website http://eudragit.evonik.com/product/eudragit/Documents/evonik-brochure-eudragit-product.pdf].*
Evonik Technical Information note [downloaded on Jul. 16, 2014 from the website http://eudragit.evonik.com/product/eudragit/Documents/evonik-specification-eudragit-e-100-e-po-e-12,5.pdf].*

(Continued)

*Primary Examiner* — Sue Liu
*Assistant Examiner* — Thor Nielsen
(74) *Attorney, Agent, or Firm* — Cooley LLP

(57) ABSTRACT

The present invention is directed to pharmaceutical compositions comprising a plurality of taste-masked non-opioid analgesic/opioid analgesic drug-containing microparticles, dosage forms comprising such pharmaceutical compositions (such as an orally disintegrating tablet), and methods of making the pharmaceutical compositions and dosage forms of the present invention. Dosage forms comprising the pharmaceutical compositions of the present invention are improved homogeneous blends of non-opioid and opioid analgesics which provide for more convenient and palatable administration of drug combinations, for example for treating pain.

44 Claims, 4 Drawing Sheets

Cross-section of a High-dose/low-dose drug combo

(56) References Cited

U.S. PATENT DOCUMENTS

2005/0084536 A1    4/2005   Van Buitenen et al.
2006/0205674 A2    9/2006   Satyam et al.
2007/0036861 A1*   2/2007   Oury et al. .................. 424/472
2008/0124398 A1    5/2008   Venkatesh et al.
2010/0330150 A1   12/2010   Venkatesh et al.

FOREIGN PATENT DOCUMENTS

WO       WO 99/13799 A1    3/1999
WO   WO 2004/069135 A2   8/2004
WO   WO 2008/015220 A1   2/2008
WO    WO 2008015221 A2 *   2/2008

OTHER PUBLICATIONS

International Search Report based on International Application No. PCT/US2010/033392, mailed on Jul. 6, 2010.
Written Opinion of the International Searching Authority based on International Application No. PCT/US2010/033392, mailed on Jul. 6, 2010.
Eudragit E100 specification sheet, 4 pages (2004).
International Search Report, PCT Appl. No. PCT/US2010/033389, 2 pages (Nov. 5, 2010).
Supplementary European Search Report, EP Appl. No. 10770481.9, 11 pages (Oct. 31, 2012).
Supplementary European Search Report, EP Appl. No. 10770482.7, 11 pages (Oct. 31, 2012).
Written Opinion of the International Searching Authority, PCT Appl. No. PCT/US2010/033389, 7 pages (Nov. 5, 2010).

* cited by examiner

ORALLY DISINTEGRATING TABLET COMPOSITIONS COMPRISING COMBINATIONS OF NON-OPIOID AND OPIOID ANALGESICS

CROSS REFERENCE TO RELATED APPLICATIONS

The present application claims priority to U.S. Provisional Application Nos. 61/174,780 and 61/174,788, both filed May 1, 2009.

BACKGROUND OF THE INVENTION

Moderate to severe pain can be effectively treated with opioid analgesics such as hydrocodone. However since many opioids are habit forming, the risk of abuse can be moderated by combining the opioid with a non-opioid analgesic, e.g. acetaminophen or an NSAID such as, aspirin, ibuprofen, etc., thereby allowing effective pain management at lower doses of the opioid analgesic. However, the need to administer multiple dosage forms can result in problems such as patient compliance issues or dosage errors.

One approach to preventing such problems is to combine multiple analgesics (e.g., the combination of non-opioid and opioid analgesics) into a single dosage form in order to minimize the number of different dosage forms administered, and to ensure that the combination of analgesics are administered in the correct relative dosages. For example, Vicodin® is an immediate-release (IR) tablet containing 5 mg of hydrocodone bitartrate and 500 mg of acetaminophen, intended for the management of severe pain. However, it is very difficult to reproducibly prepare homogeneous blends of hydrocodone and acetaminophen at the required 1:100 weight ratio (e.g., with a content uniformity having an RSD of 6% or less as required by regulatory agencies worldwide). Thus, there is a need for methods for uniformly and reproducibly combining a high-dose of non-opioid analgesic and a low-dose opioid analgesic into a single dosage form.

The two most widely used types of oral dosage forms are tablets and capsules. However, such dosage forms have several disadvantages. For example, it is estimated that 50% of the population have problems swallowing tablets (see Seager, Journal of Pharmacol. and Pharm. 50, pages 375-382, 1998). It is especially hard for the elderly or for children to swallow tablets or capsules, or to medicate patients who are unable or unwilling to swallow tablets or capsules. Furthermore, conventional tablets or capsules usually must be administered with water, which is not always possible or convenient. This leads to poor or even non-compliance with the treatment which consequently has a negative impact on the efficacy of the treatment. Orally disintegrating tablet (ODT) dosage fauns have been introduced to address such problems, because ODTs rapidly dissolve or disintegrate in the buccal cavity and the resulting slurry or suspension of the drug is more readily swallowed by the patient. Such dosage forms are also more convenient because they need not be administered with water.

Because the ODT dosage form disintegrates in the oral cavity of the patient, the disintegrated ODT must be palatable. For example, if one or more of the analgesic drugs in the ODT are bitter tasting, the drug-containing particles comprising the ODT must be taste-masked, e.g., by coating the drug-containing particles with a polymeric membrane to prevent release of the drug in the oral cavity. However, the main drawback of taste-masking is slower dissolution of the drug(s) from effectively taste-masked microparticles. The more bitter the drug, the thicker the taste-masking coating required and hence, the slower the drug release from the taste-masked drug-containing particles. Thus the very process of effectively taste-masking the drug-containing particles results in a substantially slower drug release, with concomitant slower systemic absorption of the drug in the gastrointestinal tract.

In some cases, slower drug release is a particular problem for ODT dosage forms which are intended to be bioequivalent to a reference listed immediate-release (IR) dosage form of the drug, for example bioequivalent to conventional tablet or effervescent tablet based IR dosage foams having a $T_{max}$, of less than an hour, and rapid-onset of action. For such bioequivalent immediate release ODT products, it is essential that the taste-masking layer should not substantially lower the release rate of the drug. For ODT compositions containing combinations of two or more analgesic drugs (e.g., a non-opioid/opioid analgesic formulation) this problem is particularly acute, because the different analgesic drug components of the combination ODT may require different levels of taste-masking depending on the degree of bitterness of the drugs (i.e., analgesics with low bitterness levels may require little or no taste-masking, while highly bitter analgesics may require substantial taste-masking layers). Adding further complication, taste-masking layers reduce the release rate of poorly soluble analgesic drugs more than for more soluble drugs. In certain cases, an ODT composition comprising taste-masked opioid analgesic particles combined with sustained release coated non-opioid analgesic particles may be more desirable.

In addition, ODTs must rapidly disintegrate on contact with the saliva in the oral cavity while also providing sufficient tablet hardness and strength sufficient to withstand attrition during packaging, storage, transportation, distribution, and end use, and also provide acceptable organoleptic properties (e.g., be palatable as described above, and exhibit a smooth (non-gritty) mouthfeel), and acceptable pharmacokinetic properties (i.e., rapid onset, $C_{max}$, AUC properties similar to the reference listed drugs). Achieving all of these properties is often quite difficult because thicker taste-masking layers may be required for adequate taste-masking of more soluble and/or more bitter drugs, which may make it difficult to obtain the required rapid drug release.

Thus, the preparation of clinically effective pharmaceutical compositions comprising a non-opioid analgesic and an opioid analgesic, particularly in the form of an ODT, is quite difficult and requires the balancing of many different and often competing requirements.

SUMMARY OF THE INVENTION

In one embodiment, the present invention is directed to a pharmaceutical composition comprising a plurality of modified-release coated high-dose non-opioid/low-dose opioid analgesic drug-containing microparticles, wherein the drug-containing microparticles comprise:

(a) a core comprising a high-dose non-opioid analgesic drug;
(b) a first coating disposed over the core, comprising an opioid analgesic drug; and
(c) a second coating disposed over the core, comprising a modified-release coating (e.g., a taste-masking or sustained release coating to achieve taste-masking and/or extended/sustained release properties), comprising a water-insoluble polymer.

In another embodiment, the present invention is directed to a pharmaceutical composition comprising a plurality of taste-masked non-opioid analgesic drug/opioid analgesic drug-containing microparticles, wherein the drug-containing microparticles comprise:

(a) a core comprising a high dose of a non-opioid analgesic drug such as acetaminophen;
(b) a first layer comprising a low dose of an opioid analgesic drug such as hydrocodone disposed over the high-dose non-opioid analgesic drug-containing core; and
(c) at least one modified-release coating layer (e.g., a taste-masking or sustained release coating layer) disposed over the non-opioid analgesic/opioid analgesic drug-containing core, wherein the at least one modified-release coating layer (e.g., a taste-masking or sustained release coating to achieve taste-masking and/or extended/sustained release properties), comprises a water-insoluble polymer, or the combination of a water-insoluble polymer and a water-soluble polymer or a gastrosoluble pore-former.

In still another embodiment, the present invention is directed to a pharmaceutical composition comprising a plurality of modified-release coated non-opioid analgesic/opioid analgesic drug-containing microparticles in combination with a second population of non-opioid analgesic drug-containing microparticles, wherein the modified-release coated high-dose non-opioid/low-dose opioid drug-containing microparticles comprise:

(a) a core comprising a non-opioid analgesic drug;
(b) an optional sealant coat disposed over the high-dose drug-containing core;
(c) a sustained-release coating layer disposed over the non-opioid analgesic drug-containing core;
(d) an opioid analgesic drug layer disposed over the sustained-release coating layer;
(e) an optional sealant coat disposed over the opioid analgesic drug layer; and
(f) a taste-masking layer disposed over the sealant coat;

wherein the sustained-release coating layer comprises a water-insoluble polymer optionally in combination with a water soluble or enteric polymer, thereby imparting taste-masking and/or sustained release properties to the non-opioid analgesic drug-containing particles; and the taste-masking layer disposed over the sealant coat comprises a water-insoluble polymer optionally in combination with a gastrosoluble pore-former.

In yet another embodiment, the present invention is directed to a pharmaceutical composition comprising a plurality of modified-release coated non-opioid analgesic drug particles in combination with modified-release coated non-opioid analgesic/opioid analgesic drug-containing microparticles, wherein the modified-release coated non-opioid analgesic/opioid analgesic drug-containing microparticles comprise:

(a) a core comprising a non-opioid analgesic drug;
(b) an optional sealant coat disposed over the non-opioid analgesic drug-containing core;
(c) a taste-masking coating layer disposed over the sealant coating layer;
(d) an opioid analgesic drug layer disposed over the taste-masking coating layer;
(e) a sealant coat disposed over the opioid analgesic drug layer; and
(f) a flavorant layer disposed over the sealant coat.

In still yet another embodiment, the present invention is directed to an ODT dosage form comprising the combination of one of the pharmaceutical compositions of the present invention, rapidly dispersing microgranules, and optionally a second population of non-opioid analgesic drug-containing particles comprising a non-opioid analgesic drug-containing core coated with a modified-release coating layer.

In a further embodiment, the present invention is directed to a method for preparing the pharmaceutical compositions disclosed herein, comprising:

(1) preparing cores comprising a non-opioid analgesic drug;
(2) coating the non-opioid analgesic drug-containing cores of step (1) with an opioid analgesic drug layer, thereby forming non-opioid analgesic/opioid analgesic drug-containing microparticles; and
(3) coating the non-opioid analgesic drug-containing cores of step (1) and/or the non-opioid analgesic/opioid analgesic drug-containing microparticles of step (2) with a coating layer comprising a water-insoluble polymer, thereby forming taste-masked and/or sustained-release non-opioid analgesic/opioid analgesic drug-containing microparticles.

In a further embodiment, the present invention is directed to a method for preparing an ODT pharmaceutical composition as disclosed herein, further comprising:

(1) preparing rapidly dispersing microgranules comprising a sugar alcohol, a saccharide, or a mixture thereof with an average particle size of not more than 30 μm and a super disintegrant;
(2) preparing a blend comprising non-opioid analgesic/opioid analgesic drug-containing microparticles with non-opioid analgesic drug-containing microparticles and rapidly dispersing microgranules
(3) compressing the blend into orally disintegrating tablets.

In a still further embodiment, the present invention is directed to a method of treating pain in a patient, comprising administering a therapeutically effective amount of the non-opioid analgesic and opioid analgesic-containing compositions of the present invention to the patient in need thereof.

DETAILED DESCRIPTION OF THE INVENTION

Figure 1:
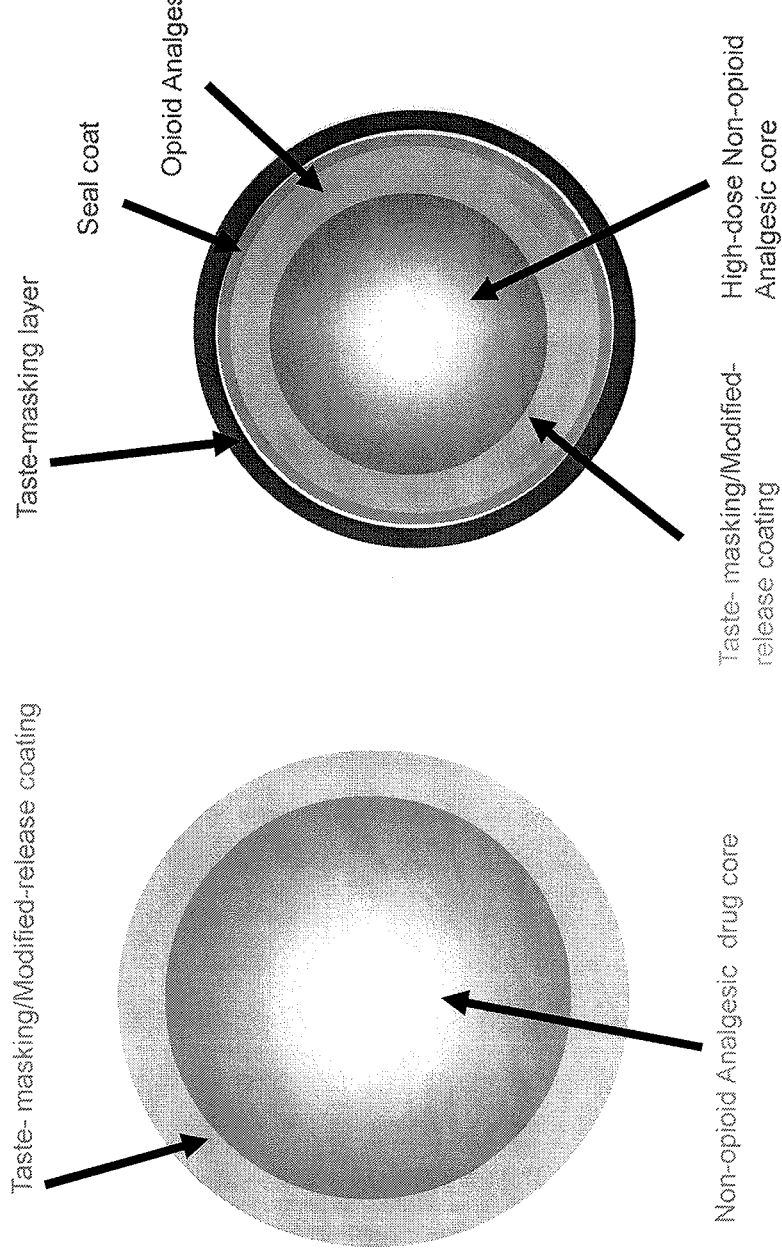
FIG. 1 illustrates a schematic of one embodiment of a modified-release (taste-masked and/or sustained release coated), high-dose, non-opioid analgesic drug-containing microparticle or a modified-release coated, low-dose opioid/high-dose non-opioid analgesic drug microparticle.

All documents cited herein are incorporated by reference in their entirety for all purposes. The citation of any document is not to be construed as an admission that it is prior art with respect to the present invention.

The present invention is directed to pharmaceutical compositions comprising a plurality of modified-release coated non-opioid analgesic/opioid analgesic drug-containing microparticles as described herein. The compositions of the present invention provide combination non-opioid/opioid analgesic drug-containing oral dosage forms meeting one or more of the following specifications:
- modified-release (i.e., taste-masked and/or sustained release) coated microparticles wherein the opioid analgesic is layered onto non-opioid analgesic drug-containing microparticles having a blend homogeneity meeting United States Pharmacopoeia requirements;
- effectively taste-masked microparticles, irrespective of the differences in solubility and bitterness of the non-opioid and opioid analgesics;
- in some embodiments the compositions of the present invention further comprise rapidly dispersing granules, thereby providing an ODT dosage form which rapidly disintegrates on contact with saliva in the oral cavity, and forms a smooth, easy-to-swallow suspension containing taste-masked analgesic drug-containing particles;
- analgesic drug-containing particles with an average particle diameter of not more than about 400 µm to provide a smooth mouthfeel leaving no aftertaste (i.e., little or minimal drug release with a non-gritty or non-chalky taste) until swallowed;
- providing rapid, substantially-complete release of the dose from immediate-release analgesic drug-containing drug particles upon arrival in the stomach, thereby enhancing the probability of being bioequivalent to the corresponding immediate-release reference-listed-drug product(s), or providing a target release profile of the non-opioid analgesic suitable for a once- or twice-daily dosing regimen; and
- providing robust tablet formulations exhibiting acceptable tablet hardness and friability suitable for packaging in HDPE bottles, and/or transportation in bulk or as packaged tablets for commercial distribution and end-use.

The term "drug", "active" or "active pharmaceutical ingredient" as used herein includes a pharmaceutically acceptable and therapeutically effective compound, pharmaceutically acceptable salts, stereoisomers and mixtures of stereoisomers, solvates (including hydrates), polymorphs, and/or esters thereof. When referring to a drug in the descriptions of the various embodiments of the invention, the reference encompasses the base drug, pharmaceutically acceptable salts, stereoisomers and mixtures of stereoisomers, solvates (including hydrates), polymorphs, and/or esters thereof, unless otherwise indicated.

The term "analgesic" refers to a drug which has pain killing or pain relieving properties.

The terms "layer" or "coating" as used herein are synonymous. For example, the terms sealant layer, drug layer, etc., are synonymous with sealant coating, drug coating, etc.

The terms "orally disintegrating tablet" or "ODT" refers to a tablet which disintegrates rapidly in the oral cavity of a patient after administration, without the need for chewing. The rate of disintegration can vary, but is faster than the rate of disintegration of conventional solid dosage forms (e.g., tablets or capsules) which are intended to be swallowed immediately after administration, or chewable solid dosage forms. Orally disintegrating compositions of the present invention can contain pharmaceutically acceptable ingredients which swell, dissolve or otherwise facilitate the disintegration or dissolution of the ODT composition. Such ingredients can include a pharmaceutical disintegrant such as crospovidone, a water-soluble sugar alcohol such as mannitol, a saccharide such as lactose, or a mixture thereof, a water-soluble binder such as povidone, a meltable solid (e.g., a hydrophobic wax such as polyethylene glycol, glyceryl behenate, stearic acid, etc.) which can release the drug(s) upon entering the stomach. Orally disintegrating compositions of the present invention may be in the form of a tablet, a minitablet, a capsule or a monodose sachet, or a dry powder for reconstitution.

The term "about", as used herein to refer to a numerical quantity, includes "exactly". For example, "about 60 second" includes 60 seconds, exactly, as well as values close to 60 seconds (e.g., 50 seconds, 55 seconds, 59 seconds, 61 seconds, 65 seconds, 70 seconds, etc.).

Unless stated otherwise, the amount of the various coatings or layers described herein (the "coating weight") is expressed as the percentage weight gain of the particles or beads provided by the dried coating, relative to the initial weight of the particles or beads prior to coating. Thus, a 10% coating weight refers to a dried coating which increases the weight of a particle by 10%.

As used herein, the term "immediate-release" or IR refers to release of greater than or equal to about 50%, or greater than about 75%, or greater than about 90%, or greater than about 95% of the drug within about 2 hours, more particularly within about one hour following administration of the dosage form.

The term "substantially disintegrates" means a level of disintegration amounting to disintegration of at least about 50%, at least about 60%, at least about 70%, at least about 80%, at least about 90%, or about 100% disintegration of the ODT composition.

As used herein, the term "modified-release" coating encompasses coatings that delay release, sustain release, extend release, prevent release, and/or otherwise prolong the release of the analgesic drug relative to formulations lacking such coatings which release the analgesic drug relatively quickly (i.e., "immediate release" compositions). The term "controlled-release" encompasses "sustained release," "extended release," "delayed release," and "timed, pulsatile release." The term "lag-time" coating refers to a particular type of "controlled release" coating in which the lag time coating delays release of a drug after administration. The term "controlled release" is also used interchangeably with "modified release." The term "controlled-release particle" refers to a particle showing one or more controlled-release properties, as described herein. The term "controlled-release particle" also refers to a drug-containing particle coated with one or more controlled-release coatings, as described herein.

The term "substantially masks the taste" in reference to the taste-masking layer of the IR particles (when present) refers to the ability of the taste-masking layer to substantially prevent release of a bitter tasting analgesic drug in the oral cavity of a patient. A taste-masking layer which "substantially masks" the taste of the analgesic drug typically releases less than about 10% of the analgesic drug in the oral cavity of the patient, in other embodiments, less than about 5%, less than about 1%, less than about 0.5%, less than about 0.1%, less than about 0.05%, less than about 0.03%, less than about 0.01% of the analgesic drug. The taste-masking properties of the taste-masking layer of the compositions of the present invention can be measured in vivo (e.g., using conventional organoleptic testing methods known in the art) or in vitro (e.g., using dissolution tests as described herein). The skilled artisan will recognize that the amount of analgesic drug release associated with a taste-masking layer than "substantially masks" the taste of the analgesic drug is not limited to the ranges expressly disclosed herein, and can vary depending on other factors, such as the perceived the bitterness of the analgesic drug and the presence of other flavoring agents in the composition.

The term "substantially modifies release" in reference to a layer refers to the ability of the layer to provide modified release properties, i.e., delay release, sustain release, extend release, prevent release, and/or otherwise prolong the release of an analgesic drug relative to formulations lacking such coatings which release a drug relatively quickly (i.e., "immediate release" compositions), as described herein.

As used herein, the term "sustained-release" (SR) refers to the property of slow release of an analgesic drug from a drug-containing core particle, without an appreciable lag time. The term "sustained-release coating" or "SR coating" refers to a coating showing sustained-release properties. The term "sustained-release particle" refers to an analgesic drug-containing particle showing sustained-release properties. In one embodiment, a sustained-release coating comprises a water-insoluble polymer and optionally a water-soluble polymer or a hydrophobic wax. An SR coating can optionally contain a plasticizer or other ingredients that do not interfere with the "sustained-release" properties of the coating.

As used herein, the term "timed, pulsatile release" (TPR) refers to the property of modified release of a drug after a pre-determined lag time. The term "timed, pulsatile-release coating" or "TPR coating" refers to a coating showing timed, pulsatile-release properties. The term "timed, pulsatile-release particle" refers to an analgesic drug-containing particle showing timed, pulsatile-release properties. In some embodiments, a lag time of from at least about 2 to about 10 hours is achieved by coating the particle with, e.g. a combination of at least one water-insoluble polymer and at least one enteric polymer (e.g., a combination of ethylcellulose and hypromellose phthalate). A TPR coating can optionally contain a plasticizer or other ingredients which do not interfere with the "timed, pulsatile release" properties of the coating.

The term "modified-release coated drug-containing microparticles" refers generally to drug-containing microparticles (e.g., crystals, granules, pellets produced by controlled spheronization, or drug layered particles/beads) coated with one or more functional polymers to provide effective taste-masking and/or extended/sustained release properties. With respect to the high-dose non-opioid analgesic/low-dose opioid analgesic drug-containing microparticles, this term refers to modified-release coated high-dose non-opioid analgesic/low-dose opioid analgesic drug-containing microparticles as described herein.

The terms "plasma concentration—time profile", "$C_{max}$", "AUC", "$T_{max}$", and "elimination half life" have their generally accepted meanings as defined in the FDA Guidance to Industry: Bioequivalence.

Unless otherwise indicated, all percentages and ratios are calculated by weight based on the total composition.

The term "disposed over" means that a second material is deposited over a first material, wherein the second material may or may not be in direct physical contact with the first material. Thus it is possible, but not necessary, that an intervening material lies between the first and second materials.

Combination drug therapies are increasingly useful in treating pain. For example, pain treatments benefit from the administration of low doses of opioid analgesics combined with relatively high-doses of non-opioid analgesics (e.g., an NSAID), which effectively treat moderate to severe pain, yet reduce the amount of potentially habit forming opioid drug administered. However, the need to administer multiple dosage forms, each containing a either an opioid or a non-opioid analgesic, can result in problems such as reduced patient compliance, errors in administering the proper doses of each drug, etc. It is therefore beneficial in such situations to prepare a single dosage form combining the two (or more) analgesics, thereby permitting the administration of a single dosage form rather than two (or more) dosage forms. However, it can be difficult to prepare such combination analgesic formulations, when one of the analgesics (e.g., a non-opioid analgesic) is present in a relatively high concentration compared to one or more of the other analgesics (e.g., an opioid analgesic); as a practical matter it is difficult to obtain a uniform mixture of a high-dose analgesic and a low-dose analgesic, such that the high-dose analgesic and the low-dose analgesic are both reproducibly provided at their respective correct dosages.

The present invention is directed to pharmaceutical compositions comprising a plurality of taste-masked non-opioid/opioid drug-containing microparticles, each containing both the high-dose analgesic(s) (e.g., one or more non-opioid analgesics) and the low-dose analgesic(s) (e.g. one or more opioid analgesics). The core of the taste-masked non-opioid/opioid drug-containing microparticles comprises the non-opioid analgesic, and the opioid analgesic is provided in an opioid analgesic layer disposed over the non-opioid analgesic drug-containing core.

Suitable core compositions include particles of the non-opioid analgesic itself (e.g., formed by recrystallization or precipitation of the non-opioid analgesic from solution, or by milling and sieving the non-opioid analgesic, etc., such that non-opioid analgesic drug-containing particles of a desired particle size and particle size distribution are obtained). Alternatively, the core can comprise a granulate comprising particles of the non-opioid analgesic in combination one or more pharmaceutically acceptable excipients (e.g., lactose, mannitol, microcrystalline cellulose, etc.) and an optional binder, prepared by wet or dry granulation. In still other embodiments, the core can comprise extruded and spheronized particles comprising the non-opioid analgesic (e.g., in combination with suitable pharmaceutically acceptable excipients as described herein); or non-opioid analgesic pellets are produced by controlled spheronization in a Granurex VEC-35 or VEC-40 from Vector Corporation, and these pellets are coated with polymers or polymer blends providing target drug release profiles suitable for once- or twice-daily dosing regimen. In yet other embodiments, the core comprises drug-layered beads—i.e., an inert core (e.g., sugar spheres, microcrystalline cellulose, mannitol-microcrystalline cellulose, silicon dioxide, etc.) layered with the non-opioid analgesic and an optional binder. In further embodiments, the core can comprise the non-opioid analgesic in combination with pharmaceutically acceptable excipients, compressed into "minitabs" having a particle diameter in the range of about 2-5 mm. In a particular embodiment, the core comprises particles of the non-opioid analgesic. In many embodiments, the core has an average particle size of less than about 500 µm, or less than about 400 µm, or less than about 300 µm, or less than about 200 µm.

Any pharmaceutically acceptable polymeric binder which is compatible with the non-opioid analgesic and/or other components of the composition may be used in preparing the non-opioid analgesic drug-containing cores (e.g., a binder used in forming a granulate, in forming drug-layered beads, etc.). Suitable polymeric binders include for example, polymers selected from the group consisting of hydroxypropylcellulose, povidone, methylcellulose, hydroxypropyl methylcellulose, carboxyalkylcelluloses, polyethylene oxides, polysaccharides, acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch, etc.

The non-opioid analgesic drug-containing core can be coated directly with the opioid analgesic layer, or can be first coated with a sealant layer. Suitable sealant layers comprise a hydrophilic water-soluble polymer. Non-limiting examples of suitable hydrophilic polymers include hydrophilic hydroxypropyl cellulose (e.g., Klucel® LF), hydroxypropyl methylcellulose or hypromellose (e.g., Opadry® Clear or Pharmacoat™ 603), vinylpyrrolidone-vinylacetate copolymer (e.g., Kollidon® VA 64 from BASF), and ethylcellulose, e.g. low-viscosity ethylcellulose. In many embodiments, particularly when the non-opioid analgesic drug-containing core comprises particles of the non-opioid analgesic, the compositions of the present invention do not require a sealant layer coated directly over the core.

The sealant layer can be applied at a coating weight of about 1% to about 10%, for example about 1%, about 2%, about 3%, about 4%, about 5%, about 6%, about 7%, about 8%, about 9%, or about 10%, inclusive of all ranges and subranges therebetween.

In some embodiments, the compositions of the present invention are intended to disintegrate in the oral cavity of the patient upon administration (e.g., the ODT dosage form as described herein). In such embodiments, when the non-opioid analgesic and/or the opioid analgesic has unpleasant sensory properties (e.g., is bitter tasting), the non-opioid analgesic drug-containing core and/or the opioid analgesic drug-containing layer is taste-masked to prevent the patient from tasting the non-opioid and/or opioid analgesic, e.g. by coating the non-opioid analgesic drug-containing core and/or the opioid analgesic drug-containing layer with a taste-masking layer. For example, the compositions of the present invention can include a single taste-masking layer as described herein disposed between the non-opioid analgesic drug-containing core and the opioid analgesic drug-containing layer, a single taste-masking layer as described herein disposed over the opioid analgesic drug-containing layer, or two taste-masking layers disposed respectively between the non-opioid analgesic drug-containing core and the opioid analgesic drug-containing layer and over the opioid analgesic drug-containing layer. The taste-masking layer can be coated directly onto the non-opioid analgesic drug-containing core and/or the opioid analgesic drug-containing layer, or the non-opioid analgesic drug-containing core and/or opioid analgesic drug-containing layer can be first coated with a sealant layer (e.g., as described herein) for example to minimize or prevent static charging and/or particle attrition, followed by the taste-masking polymer coating. When the compositions of the present invention comprise two or more taste-masking layers, the taste-masking layers can be independently selected from any of the taste-masking layer compositions described herein.

Suitable taste-masking layers can comprise a water-insoluble polymer or the combination of a water-insoluble polymer and a gastrosoluble pore-former (e.g., gastrosoluble and pharmaceutically acceptable organic, inorganic, or polymeric materials.

The taste-masking layer can be coated onto the non-opioid analgesic drug-containing core and/or opioid analgesic drug-containing layer by any suitable method, e.g., fluid bed coating or coacervation. For example the taste-masking polymer coating can be deposited in the core to provide a weight gain (after coating and drying) of from about 3% to about 50%, including about 3%, about 5%, about 7%, about 10%, about 12%, about 15%, about 17%, about 20%, about 22%, about 25%, about 27%, about 30%, about 35%, about 40%, about 45%, or about 50%, inclusive of all ranges and subranges therebetween.

Non-limiting examples of suitable water-insoluble polymers include ethylcellulose, cellulose acetate, cellulose triacetate, cellulose acetate butyrate, polyvinyl acetate, neutral methacrylic acid-methylmethacrylate copolymers (e.g., Eudragit RL, RS, and NE30D, etc.), and mixtures thereof. In one embodiment, the water-insoluble polymer comprises ethylcellulose. In another embodiment, the water-insoluble polymer comprises ethylcellulose with a mean viscosity of 10 cps (e.g., Ethocel Standard 10 Premium) or about 100 cps (Ethocel Standard 100 Premium) in a 5% solution in 80/20 toluene/ethanol, measured at 25° C. with an Ubbelohde viscometer.

As described herein, in some embodiments the taste-masking layer(s) independently comprises the combination of a water-insoluble polymer (as described herein) in combination with gastrosoluble pore-former. Pore-formers include polymeric and non-polymeric pharmaceutically acceptable gastrosoluble materials. Non-limiting examples of non-polymeric gastrosoluble pore-formers, include pharmaceutically acceptable inorganic materials such as calcium carbonate, magnesium carbonate, calcium phosphate, ferric hydroxide, ferric phosphate, magnesium hydroxide, magnesium phosphate, etc.; pharmaceutically acceptable non-polymeric organic materials such as calcium saccharide, calcium succinate, calcium tartrate, magnesium citrate, ferric acetate, etc.; pharmaceutically acceptable gastrosoluble polymers including maltrin, aminoalkyl methacrylate copolymers available under the trade name of Eudragit® (type E100 or EPO), polyvinylacetal diethylaminoacetate e.g., AEA® available from Sankyo Company Limited, Tokyo (Japan), and the like; and mixtures thereof. In one embodiment, the gastrosoluble polymer is a terpolymer based on dimethylaminoethyl methacrylate, butyl methacrylate, and methyl methacrylate. In another embodiment, the terpolymer has an average molecular weight of 150,000 and the ratio of the monomers is 1:2:1 of methyl methacrylate, N,N-dimethylaminoethyl methacrylate, and butyl methacrylate, and mixtures thereof.

The ratio of water-insoluble polymer to gastrosoluble pore-former ranges from about 95/5 to about 50/50 including about 90/10, about 85/15, about 80/20, about 75/25, about 70/30, about 65/35, about 60/40, or about 55/45.

The coating weight of the taste-masking layer comprising a water-insoluble polymer and a gastrosoluble pore-former ranges from about 5% to about 30%, or about 5%-25%, about 5%-20%, about 5%-15%, about 5%-10%, about 10%-30%, about 10%-25%, about 10%-20%, about 10%-15%, about 15%-30%, about 50%-25%, about 15%-20%, about 20%-30%, about 20%-25%, or about 25%-30%.

The ratio of the water-insoluble polymer to the gastrosoluble polymer ranges from about 9/1 to about 1/1, including the range of about 6/3 to about 2/1. In other embodiments, the ratio of water-insoluble polymer to gastrosoluble polymer is about 95/5, about 90/10, about 85/15, about 80/20, about 75/25, about 70/30, about 65/35, about 60/40, about 55/45, or about 50/50, inclusive of all values, ranges, and subranges therebetween.

In some embodiments, the taste-masking layer comprising the combination of a water-insoluble polymer and gastrosoluble polymer has a coating weight of about 10% to about 40% by weight, including the ranges from about 12% to about 30%, about 15% to about 25%, and from about 20% to about 30%. In other embodiments, the coating weight of the taste-masking layer comprising a combination of water-insoluble and gastrosoluble polymers is about 10%, about 12.5%, about 13%, about 15%, about 17%, about 18%, about 20%, about 22%, about 24%, about 25%, about 27%, about 30%, about 35%, or about 40%, inclusive of all ranges and subranges therebetween.

In various embodiments, it is desirable to provide an extended-release coating layer over the non-opioid analgesic drug-containing cores in order to modify the release of the non-opioid analgesic. The extended-release coating disposed over the non-opioid analgesic drug-containing cores can comprise a water-insoluble polymer, thereby providing a sustained release (SR) coating; a water-insoluble polymer in combination with an enteric or water-soluble polymer, thereby providing a timed pulsatile release (TPR) coating. In still other embodiments, the extended-release coating comprises an enteric polymer disposed on the non-opioid analgesic drug-containing particle, thereby providing a delayed release (DR) coating.

In some embodiments, the extended-release coating provides suitable properties (e.g., extended release characteristics, mechanical properties, and coating properties) without the need for a plasticizer. For example, ethylcellulose without a plasticizer is used for coating drug-containing cores by solvent coacervation via phase separation for taste-masking, and or can be applied e.g. from a suitable solvent to provide sustained-release properties. Also, coatings comprising polyvinyl acetate (PVA), neutral and cationic copolymers of acrylate/methacrylate esters (e.g., NE30D and EPO), waxes, etc. can be applied without plasticizers.

Non-limiting examples of suitable enteric polymers include cellulose acetate phthalate, hydroxypropyl methylcellulose phthalate, hydroxypropyl methylcellulose acetate succinate, polyvinyl acetate phthalate, pH-sensitive methacrylic acid/methylmethacrylate copolymers (e.g., Eudragit® L, S and FS polymers), shellac, and mixtures thereof. In certain embodiments, non-polymeric enteric materials such as non-polymeric waxes and fatty acid compositions may be used instead of enteric polymers, provided they have the pH sensitive solubility associate with enteric polymers. These enteric polymers may be used as a solution in a solvent mixture or an aqueous dispersion. Some commercially available materials that may be used are methacrylic acid copolymers sold under the trademark Eudragit (L100, S100, L30D) manufactured by Rohm Pharma, Cellacefate (cellulose acetate phthalate) from Eastman Chemical Co., Aquateric (cellulose acetate phthalate aqueous dispersion) from FMC Corp., and Aqoat (hydroxypropyl methylcellulose acetate succinate aqueous dispersion) from Shin Etsu K.K.

The coating weight of the extended-release coating comprising the combination of a water-insoluble polymer and an enteric polymer ranges from about 10 to 60%, more particularly from about 30% to 60%, including about 15%, about 20%, about 25%, about 30%, about 35%, about 40%, about 45%, about 50%, or about 55%, inclusive of all ranges and sub ranges therebetween. The ratio of water insoluble polymer to enteric polymer may vary from about 10:1 to 1:2, more particularly from about 2:1 to 1:1, including about 9:1, about 8:1, about 7:1 about 6:1, about 5:1 about 4:1, about 3:1, about 2:1, or about 1:1.

In other embodiments, the extended-release layer comprises the combination of a water-insoluble polymer (as described herein) in combination with a water-soluble polymer. Non-limiting examples of suitable water-soluble polymers include polyvinylpyrrolidone (e.g., Povidone K-25), polyethylene glycol (e.g., PEG 400), hydroxypropyl methylcellulose, and hydroxypropylcellulose.

The ratio of the water-insoluble polymer to the water-soluble polymer ranges from about 95/5 to about 50/50, including ratios of about 95/5, about 90/10, about 85/15, about 80/20, about 75/25, about 70/30, about 65/35, about 60/40, about 55/45, or about 50/50, inclusive of all ranges and subranges therebetween. In other embodiments, the taste-masking layer comprising the combination of a water-insoluble polymer and a water-soluble polymer is deposited over the non-opioid analgesic drug-containing core at a coating weight of about 3%, about 5%, about 7%, about 10%, about 12%, about 15%, about 17%, about 20%, about 22%, about 25%, about 27%, about 30%, about 35%, about 40%, about 45%, and about 50% by weight, inclusive of all values, ranges, and subranges therebetween.

In some other embodiments, the present invention relates to a pharmaceutical composition comprising modified-release coated non-opioid analgesic cores comprising at least one therapeutic agent or a pharmaceutically acceptable salt, solvate, and/or ester thereof; a water-insoluble polymer (e.g., ethylcellulose), a second optional coating disposed over the first coating, comprising an enteric polymer and optionally a water-insoluble polymer (e.g., ethylcellulose and hypromellose phthalate at a ratio of from about 9:1 to about 5:5).

The modified-release or taste-masking layer can be unplasticized or plasticized. For example, drug-containing particles can be taste-masked with ethylcellulose by solvent coacervation via phase separation without requiring a plasticizer, or from suitable pharmaceutically acceptable solvent using a fluid bed coater. Modified-release coatings comprising various polymers such as Eudragit NE30D or various hydrophobic waxes in a fluid bed coater typically do not require a plasticizer.

When it is desirable or convenient to use a plasticizer, non-limiting examples of suitable plasticizers include glycerol and esters thereof (e.g., acetylated mono- or diglycerides including commercially available Myvacet® 9-45), glyceryl monostearate, glyceryl triacetate, glyceryl tributyrate, phthalates (e.g., dibutyl phthalate, diethyl phthalate, dimethyl phthalate, dioctyl phthalate, etc.), acetylcitric acid tributyl ester, acetylcitric acid triethyl ester, tributyl citrate, acetyltributyl citrate, triethyl citrate, glyceroltributyrate; diethyl sebacate, dibutyl sebacate, dibutyl adipates, dibutyl azelates, dibutyl benzoates, chlorobutanol, polyethylene glycols, vegetable oils, diethyl fumarate, diethyl malates, diethyl oxalate, dibutyl succinate, dibutyl butyrate, cetyl alcohol esters, malonates (e.g., diethyl malonate etc.), castor oils, polysorbates, N-butylbenzenesulfonamide, N-methylpyrrolidone, and mixtures thereof. In some embodiments, it is desirable to use a non-phthalate plasticizer. In various embodiments of the present invention, the amount of plasticizer in the taste-masking layer, relative to the amount of water-insoluble polymer, ranges from about 3% to about 30% by weight. In another embodiment, the amount of plasticizer ranges from 10% to about 25% by weight of the water-insoluble polymer. In still other embodiments, the amount of plasticizer relative to the weight of the water-insoluble polymer is about 3%, about 5%, about 7%, about 10%, about 12%, about 15%, about 17%, about 20%, about 22%, about 25%, about 27%, and about 30%, inclusive of all ranges and subranges therebetween. One of ordinary skill in the art would know to select the type of plasticizer based on the polymer or polymers and nature of the coating system (e.g., aqueous or solvent-based, solution or dispersion-based and the total solids). In a particular embodiment, the plasticizer is castor oil.

In some embodiments, the taste-masking layer can further comprise an anti-tacky agent to reduce aggregation of the taste-masked particles. Suitable anti-tacky agents include talc and/or magnesium stearate.

In one embodiment, the taste-masking polymer coating comprises a plasticized water-insoluble polymer, such as ethylcellulose (EC-10), at a coating weight of about 5-50% by weight.

In certain embodiments of the present invention, the low-dose opioid analgesic/high-dose non-opioid analgesic drug-containing microparticles comprise a low-dose opioid analgesic layered onto cores comprising microencapsulated non-opioid analgesic microparticles. Taste-masking of such particles is provided by a dual coating comprising an inner protective coating layer disposed over the microencapsulated high-dose non-opioid analgesic drug-containing microparticle core, and an outer coating layer disposed over the low-dose opioid analgesic layer. The inner protective coating comprises hydroxypropylcellulose, and the outer coating layer comprises a sweetener such as sucralose, coated to a total weight gain of about 15% or about 10%. The ratio of the coating weights of the inner and outer layers of the dual coating can range from about 1:1 to 1:2.

In some embodiments, the modified-release and/or taste-masked non-opioid analgesic-drug containing core is coated with a sealant layer, for example to minimize attrition or agglomeration of the taste-masked cores, or alternatively to prevent contact between the non-opioid analgesic in the core and e.g., the opioid analgesic in the opioid analgesic layer. The composition and coating weight of the sealant layer is as described herein.

The opioid analgesic layer is disposed directly over the non-opioid analgesic drug-containing core, or over a sealant coated core, and/or a taste-masked core. The opioid analgesic can be coated onto the non-opioid analgesic-drug containing core by any suitable method, e.g., pan coating or fluid bed coating using a solution of the opioid analgesic (in a pharmaceutically acceptable solvent), optionally in combination with a polymeric binder as described herein. For example, the opioid analgesic coating solution can comprise a suitable solvent (e.g. water, a pharmaceutically acceptable organic solvent such as acetone or alcohol, or aqueous organic solvents) in which the opioid analgesic and an optionally a binder (e.g., hydroxypropylcellulose, polyvinylpyrrolidone, etc.) are dissolved.

The resulting non-opioid analgesic/opioid analgesic drug-containing microparticle can then be coated, if needed, with an additional sealant layer (as described herein), and/or a taste-masking layer (also as described herein). Thus, in some embodiments, the ultimate non-opioid analgesic/opioid analgesic drug-containing microparticles comprise a non-opioid analgesic drug-containing core (as described herein), coated with an optional sealant coating, a taste-masking layer (e.g., comprising a water-insoluble polymer or a water insoluble polymer in combination with a water-soluble or gastrosoluble polymer), an opioid analgesic layer, a second optional sealant layer, and a second taste-masking layer (e.g., comprising a water-insoluble polymer or a water insoluble polymer in combination with a water-soluble or gastrosoluble polymer).

The non-opioid analgesic/opioid analgesic drug-containing microparticles can optionally comprise one or more sealant layers, wherein the sealant layers can have the same composition or different compositions, and can be coated at the same coating weight or different coating weights. Similarly, if the non-opioid analgesic/opioid analgesic drug-containing microparticles comprise two taste-masking layers, the two taste-masking layers can have the same composition or a different composition and/or the same coating weight or different coating weights. For example, the inner taste-masking layer can comprise a water-insoluble polymer, and the outer taste-masking layer can comprise the combination of a water-insoluble polymer and a water-soluble polymer and/or gastrosoluble polymer, etc.

In other embodiments, a flavorant coating layer can be disposed over the opioid analgesic drug-containing layer (e.g., instead of a taste-masking layer), such that the non-opioid analgesic/opioid analgesic drug-containing microparticles comprise, for example a non-opioid analgesic drug-containing core (as described herein), coated with an optional sealant coating, a taste-masking layer (e.g., comprising a water-insoluble polymer or a water insoluble polymer in combination with a water-soluble or gastrosoluble polymer), an opioid analgesic layer, a second optional sealant layer, and the flavorant coating layer.

The flavorant coating layer comprises a combination of a flavorant and a binder. Suitable binders include those described herein. The flavorant includes water soluble sweeteners such as sucralose, saccharine, aspartame, neotame, acesulfame K, sodium saccharinate, neohesperidine, lactitol, maltitol, sorbitol, and mixtures thereof, or alternatively flavoring agents such as strawberry cherry, peppermint, strawberry and mixtures thereof. In one embodiment, the binder is hydroxypropyl cellulose and the flavorant is sucralose.

The coating weight of the flavorant coating layer can range from about 1% to about 10% by weight, including the ranges from about 3.0% to about 8%, about 5% to about 7.5%, and from about 5% to about 10%, of the weight of the coated core, or about 1%, about 2%, about 3%, about 4%, about 5%, about 6%, about 7%, about 8%, about 9%, or about 10%, inclusive of all ranges and subranges therebetween.

As described herein, the taste-masked high-dose/opioid analgesic drug-containing microparticles can include various layers in addition to the taste-masking layer (e.g. optional sealant layers, etc.). Thus, the taste-masking layer can be disposed directly over the non-opioid analgesic drug-containing core, or a sealant layer can be interposed between the non-opioid analgesic drug-containing core and a taste-masking layer. In other embodiments, the opioid analgesic drug-containing layer is coated with a taste-masking layer comprising a water-insoluble polymer combined with a gastrosoluble polymer such as a cationic dimethylaminoethyl methacrylate copolymer. In another embodiment, the taste-masking layer disposed over the opioid analgesic layer comprises a water-insoluble polymer and no water-soluble or gastrosoluble polymer. In an alternative embodiment, a flavorant coating layer (e.g., at coating weight of about 1% to about 10%) comprising a water-soluble sweetener is disposed directly over the opioid analgesic layer, or over a sealant layer (e.g., hydroxypropyl cellulose at a coating weight of about 1% to about 10%) disposed over the opioid analgesic layer. The non-opioid analgesic/opioid analgesic drug-containing microparticles of the present invention provide rapid dissolution of the high-dose and opioid analgesics when dissolution tested using USP Apparatus 1 (baskets@ 100 RPM) or USP Apparatus 2 (paddles@ 50 RPM) in 900 mL media (pH 1.2, pH 5.8, pH 6.8, or pH 7 (water)) at 37° C.

As described herein, the pharmaceutical compositions comprising the modified-release coated non-opioid analgesic/opioid analgesic drug-containing microparticles of the present invention provide blend homogeneity as well as uniformity of dosage units as per the USP requirements which are difficult to achieve by other methods (e.g., by blending particles comprising the non-opioid analgesic with a second population of particles comprising the opioid analgesic), particularly when the ratio of the non-opioid analgesic to the opioid analgesic is about 20/1 or higher (e.g., about 20/1, about 25/1, about 30/1, about 35/1, about 40/1, about 45/1, about 50/1, about 60/1, about 70/1, about 80/1, about 90/1, about 100/1, etc.).

The non-opioid analgesic and the opioid analgesic can comprise any drugs which are intended to be used in combination to treat pain in a patient. For example, pharmaceutical compositions of the present invention can include combinations of high-dose and opioid analgesics such as non-opioid analgesics (e.g., acetaminophen and non-steroidal anti-inflammatory drugs such as aspirin, ibuprofen, ketoprofen, meloxicam, diclofenac potassium, etodolac, sulindac, indomethacin, celecoxib, etc.) in combination with one or more opioid analgesics (hydrocodone bitartrate, oxymorphone, buprenorphine, fentanyl, hydromorphone) for the treatment of moderate-to-severe pain. In a particular embodiment, the opioid analgesic is a therapeutically effective amount of hydrocodone bitartrate and the non-opioid analgesic is a therapeutically effective amount of acetaminophen for treating pain.

The pharmaceutical compositions of the present invention comprise non-opioid analgesic/opioid analgesic drug-containing microparticles. In an alternative embodiment, the pharmaceutical compositions of the present invention can further comprise a second population of non-opioid analgesic drug-containing microparticles. The non-opioid analgesic drug-containing microparticles comprise, for example, a non-opioid analgesic drug-containing core (as described herein) coated with a water-insoluble polymer, e.g., at a coating weight of about 15% to about 35%, thereby providing sustained-release (SR) non-opioid analgesic drug-containing particles. The combination of non-opioid analgesic/opioid analgesic drug-containing microparticles and SR non-opioid analgesic drug-containing particles exhibit rapid opioid analgesic drug release profiles and prolonged non-opioid analgesic drug release (modified release) profiles.

The pharmaceutical compositions of the present invention can be used to prepare oral dosage forms such as tablets, capsules, and ODTs. Tablets can be prepared by combining the pharmaceutical compositions of the present invention with suitable pharmaceutically acceptable excipients, and then compressing the resulting mixture to form tablets. Alternatively, capsules can be filled with the pharmaceutical compositions of the present invention (and optional excipients).

In a particular embodiment, the pharmaceutical compositions of the present invention can be combined with rapidly dispersing microgranules to form in an orally disintegrating tablet (ODT). An ODT is a tablet designed to substantially disintegrate in the oral cavity after administration (without chewing) within about 60 seconds after contact with saliva (i.e., in the oral cavity) or with simulated saliva fluid (e.g., tested according to the USP <701> Disintegration Test). In particular embodiments, the ODT substantially disintegrates within about 30 seconds. The disintegration of the ODT in the oral cavity of the patient provides a smooth, easy-to-swallow suspension having no gritty mouthfeel or aftertaste, while still providing pharmacokinetic profiles for the drugs contained in the ODT (e.g., plasma concentration vs. time profiles) which are bioequivalent to the respective reference listed drugs (RLDs).

The ODTs of the present invention comprise the pharmaceutical compositions of the present invention combined with rapidly dispersing microgranules. Rapidly dispersing microgranules can be prepared as described in US Publication Nos. 2006/0078614, 2006/0105038, 2005/0232988 or 2003/0215500 (each of which is herein incorporated by reference in its entirety for all purposes) by granulating a disintegrant with a sugar alcohol and/or saccharide having an average particle size of not more than about 30 μm. The granulation can be carried out, for example, in a high shear granulator with approximately 20-25% water as the granulating fluid, and if needed wet milled and dried to produce rapidly dispersing microgranules, for example having an average particle size of not more than about 300 μm (e.g., about 175-300 μm).

The ratio of the disintegrant to the sugar alcohol, saccharide, or mixture thereof in the rapidly dispersing microgranules ranges from about 90/10 to about 99/01, for example about 90/10, about 91/9, about 92/8, about 93/7, about 94/6, about 95/5, about 96/4, about 97/3, about 98/2, about 99/1, inclusive of all values, ranges, and subranges therebetween.

The ratio of the rapidly dispersing microgranules to taste-masked analgesic drug-containing particles ranges from about 5/1 to about 1/1, including about 5/1, 4/1, 3/1, 2/1, 1/1, inclusive of all values, ranges, and subranges therebetween.

The taste-masked non-opioid analgesic/opioid analgesic drug-containing microparticles incorporated into the ODT dosage form should also have a small enough particle size such that after disintegration of the ODT in the oral cavity of the patient, a smooth, easy-to-swallow suspension results. In most embodiments in which the pharmaceutical compositions of the present invention as provided as an ODT dosage form, the average particle size of the taste-masked non-opioid analgesic/opioid analgesic drug-containing microparticles is not more than about 400 μm, or in some embodiments not more than about 300 μm.

The ODT dosage form, as described herein, may also include pharmaceutically acceptable excipients typically used in disintegrating tablet formulations such as microcrystalline cellulose and spray dried mannitol (compressible diluents), croscarmellose sodium or crospovidone (super disintegrant), coloring agents, and optionally magnesium stearate or sodium stearyl fumarate (lubricant intragranularly mixed or used externally to lubricate die and punch surfaces).

Tablet dosage forms, including ODT dosage forms, comprising the pharmaceutical composition of the present invention have a low friability, e.g., less than about 1%, (e.g., less than about 0.9%, less than about 0.8%, less than about 0.7%, less than about 0.6%, less than about 0.5%, less than about 0.4%, less than about 0.3%, etc., inclusive of all ranges and subranges therebetween) in order to have sufficient durability to withstand handling, shipping, and/or packaging in push-through blister packaging.

A non-limiting list of suitable disintegrants for the rapidly dispersing microgranules includes crospovidone (cross-linked PVP), sodium starch glycolate, cross-linked sodium carboxymethylcellulose, calcium silicate, and low substituted hydroxypropyl cellulose. The amount of disintegrant in the ODT is typically in the range of about 1% to about 10% by weight, including about 1%, about 2%, about 3%, about 4%, about 5%, about 6%, about 7%, about 8%, about 9%, or about 10%, inclusive of all ranges and subranges therebetween. In a particular embodiment, the disintegrant for the rapidly dispersing microgranules is selected from the group consisting of crospovidone, cross-linked sodium carboxymethylcellulose, and low substituted hydroxypropyl cellulose. In a more particular embodiment, the disintegrant for the rapidly dispersing microgranules is crospovidone.

A non-limiting list of suitable sugar alcohols includes mannitol, sorbitol, xylitol, maltitol, arabitol, ribitol, dulcitol, iditol, isomalt, lactitol, erythritol and combinations thereof. In a particular embodiment, the sugar alcohol is mannitol. A non-limiting list of suitable saccharides includes lactose, sucrose, maltose, and combinations thereof. In a particular embodiment, the saccharide is lactose. The amount of sugar alcohol and/or saccharide in the ODT ranges from about 30% to about 70% by weight, including, for example, about 30%, about 35%, about 40%, about 45%, about 50%, about 55%, about 60%, about 65%, or about 70%, inclusive of all ranges and subranges therebetween.

Pharmaceutically acceptable excipients include fillers, diluents, glidants, disintegrants, binders, lubricants etc. Other pharmaceutically acceptable excipients include acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents etc.

Examples of suitable fillers, diluents and/or binders include lactose (e.g. spray-dried lactose, α-lactose, β-lactose, Tabletose®, various grades of Pharmatose®, Microtose® or Fast-Flo®), microcrystalline cellulose (various grades of Avicel®, Ceolus®, Elcema®, Vivacel®, Ming Tai® or Solka-Floc®), hydroxypropylcellulose, L-hydroxypropylcellulose (low substituted), low molecular weight hydroxypropyl methylcellulose (HPMC) (e.g. Methocel E, F and K from Dow Chemical, Metolose SH from Shin-Etsu, Ltd), hydroxyethylcellulose, sodium carboxymethylcellulose, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Examples of suitable diluents include e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Examples of suitable disintegrants include e.g. alginic acid or alginates, microcrystalline cellulose, hydroxypropyl cellulose and other cellulose derivatives, croscarmellose sodium, crospovidone, polacrilin potassium, sodium starch glycolate, starch, pregelatinized starch, carboxymethyl starch (e.g. Primogel® and Explotab®) etc.

Specific examples of glidants and lubricants include stearic acid, magnesium stearate, calcium stearate or other metallic stearates, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients include e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

The present invention is also directed to methods of preparing the pharmaceutical compositions and dosage forms described herein. In one embodiment, the non-opioid/opioid analgesic drug-containing microparticles are prepared by a method comprising:
(a) preparing a core comprising a non-opioid analgesic as described herein (e.g., a non-opioid analgesic such as acetaminophen, diclofenac potassium, etc.);
(b) coating an opioid analgesic layer (e.g., comprising an opioid analgesic as described herein, such as hydrocodone bitartrate) over the non-opioid analgesic drug-containing core;
(c) coating the non-opioid analgesic drug-containing core of step (a) with at least one taste-masking and/or modified-release coating layer and the non-opioid/opioid analgesic drug-containing particles of step (b) with at least one taste-masking layer or sweetener or flavorant layer.

The step (a) of preparing the core may be accomplished by any of the methods known in the art; for example, layering an inert bead (e.g., sugar, microcrystalline cellulose, mannitol-microcrystalline cellulose, silicon dioxide, etc.) with a solution comprising the non-opioid analgesic drug and optionally a polymeric binder (e.g., by fluid-bed or pan coating). Alternatively, the core may comprise non-opioid analgesic drug crystals of the desired particle size (e.g., about 50-500 µm, including 100-250 µm), prepared by crystallization of the non-opioid analgesic drug from a suitable solvent, or by milling the non-opioid analgesic drug crystals to a desired particle size. In still other embodiments, the core can comprise a pellet prepared by controlled-spheronization.

In a particular embodiment, the microgranules comprising a non-opioid analgesic drug may be prepared by a conventional high-shear or planetary granulation process or non-opioid analgesic drug-containing pellets may be prepared by a conventional granulation-extrusion-spheronization process comprising e.g. acetaminophen, a polymer binder and one or more fillers/diluents.

Step (b) comprises coating the taste-masked non-opioid analgesic drug-containing core with the opioid analgesic drug using a drug-layering solution as described herein (e.g., comprising a solution of the opioid analgesic and optionally a binder). The opioid analgesic layer can be applied using any suitable method, for example fluid bed, pan coating, coacervation, etc.

Step (c) comprises coating the non-opioid analgesic drug-containing core and/or the opioid analgesic containing layer with a taste-masking layer. In some embodiments, a taste-masking layer is coated directly over the non-opioid analgesic drug-containing core, or a sealant layer is coated onto the non-opioid analgesic drug-containing core before coating with the opioid analgesic drug-containing layer and/or a taste-masking layer. Likewise, a sealant layer may be coated onto the opioid analgesic drug-containing layer before coating with a taste-masking layer or a flavorant layer as described herein (e.g., comprising a sweetener and/or flavoring agent and an optional polymeric binder such as hydroxypropylcellulose, applied as a solution or suspension). The taste-masking layer comprises a water-insoluble polymer or a water-insoluble polymer combined with a water-soluble or gastrosoluble polymer (and optionally a binder), for example any of the compositions described herein such as ethylcellulose (Ethocel Standard 100 Premium, at a coating weight of about 10%), or a combination of ethylcellulose with a gastrosoluble polymer (e.g., Eudragit E100) at coating weight of about 25%.

After depositing the opioid analgesic drug layer, the resulting particles can optionally be coated with a sealant coat (as described herein) and then coated with a taste-masking layer or flavorant layer (as described herein). For example, the taste-masking layer applied over the opioid analgesic drug layer (or over a sealant coat deposited on the opioid analgesic drug layer) can comprise a water-insoluble polymer (e.g. ethylcellulose) or the combination of a water-insoluble polymer and a water soluble or gastrosoluble polymer (e.g., ethylcellulose in combination with Eudragit E100). Alternatively, instead of a taste-masking layer, a flavorant coating can be applied over the opioid analgesic layer, or over a sealant layer applied to the opioid analgesic layer.

In particular embodiments, the method comprises coating by solvent coacervation a taste-masking layer directly over the non-opioid analgesic drug-containing core or over a sealant layer disposed on the non-opioid analgesic drug-containing core, wherein the taste-masking layer comprises water-insoluble ethylcellulose (Ethocel Standard 100 Premium) at coating weight of about 6%. In other embodiments, the method comprises coating water-insoluble ethylcellulose (Ethocel Standard 10 Premium) in combination with water-soluble hydroxypropylcellulose at a ratio of 7:3 or gastrosoluble Eudragit E100 at a ratio of 8:7 at a coating weight of about 20% by fluid bed coating.

In another particular embodiment, the method comprises coating by solvent coacervation a taste-masking layer directly over the opioid analgesic drug-containing layer or over a sealant layer disposed on the opioid analgesic drug-containing layer, e.g. with water-insoluble ethylcellulose (Ethocel Standard 100 Premium) at a coating weight of about 6%. In other embodiments, the method comprises coating water-insoluble ethylcellulose (Ethocel Standard 10 Premium) in combination with water-soluble hydroxypropylcellulose at a ratio of 7:3 or gastrosoluble Eudragit E100 at a ratio of 8:7 at a level of about 20% by weight based on the total weight of the coated particles by fluid bed coating. Taste-masking coatings can be prepared and applied as described, for example in U.S. Patent Publ. Nos. 2006/0078614 and 2006/0105039.

In yet another particular embodiment, the method comprises coating the opioid analgesic drug-containing layer with a sealant layer comprising hydrophilic hydroxypropylcellulose at a coating weight of about 5%, then coating with a taste-masking layer comprising a sweetener such as sucralose at a coating weight of about 5% by weight.

The ultimate dosage form comprising the taste-masked non-opioid analgesic/opioid analgesic drug-containing microparticles of the present invention can then be prepared by various methods known in the pharmaceutical arts, such as filling an appropriate amount of the taste-masked non-opioid analgesic/opioid analgesic drug-containing microparticles into e.g. a gelatin capsule or a container suitable for storing a suspension, sachet, etc. In other embodiments, the taste-masked non-opioid analgesic/opioid analgesic drug-containing microparticles of the present invention are combined with suitable pharmaceutically acceptable excipients and compressed to form a tablet. Tablets comprising the pharmaceutical compositions of the present invention can contain an internal lubricant (e.g., magnesium stearate), or can be compressed into tablets using an external lubrication process, in which the lubricant is sprayed onto the surface of the die and punch surfaces, rather than incorporated into the compression blend. External lubrication and compression methods than can be used to prepare oral dosage forms (e.g., tablets, ODTs) comprising the pharmaceutical compositions of the present invention are described for example in U.S. Pat. Nos. 5,996,902 and 6,776,361.

When the ultimate dosage form is an ODT, the method further comprises preparing rapidly dispersing microgranules comprising a disintegrant and a sugar alcohol, a saccharide or a mixture thereof, wherein each of the disintegrant, sugar alcohol and/or saccharide have an average particle diameter of not more than 30 μm; then combining the rapidly dispersing microgranules with taste-masked non-opioid analgesic/opioid analgesic drug-containing microgranules and optionally other pharmaceutically acceptable excipients, e.g., in a mixer or V-blender; and finally compressing the blend of rapidly dispersing microgranules and taste-masked non-opioid analgesic/opioid analgesic drug-containing microgranules into an ODT, e.g., using an externally lubricated tablet press to provide ODTs with desired tableting characteristics (e.g., adequate hardness, friability of <0.6%, low disintegration time, and rapid dissolution). Rapidly dispersing microgranules can be prepared following the procedures disclosed in US Patent Publ. Nos. 2006/0078614, 2006/0105038, U.S. 20050232988, and 20030215500 (each of which is herein incorporated by reference in its entirety for all purposes).

In particular embodiments, the rapidly dispersing microgranules and taste-masked analgesic drug-containing microparticles may be present in the ratio of about 4/1 to 2/1 to achieve a smooth mouthfeel. Rapidly dispersing microgranules may be produced as described herein by granulating a disintegrant such as Crospovidone XL-10 with a sugar alcohol or a saccharide, or a combination thereof, each having an average particle diameter of not more than about 30 μm, with water or an alcohol-water mixture in a conventional or high shear granulator and drying in a fluid bed equipment or a tray drying oven to produce granules with an average particle size not more than about 400 μm (preferably not more than about 300 μm).

The ultimate dosage form can comprise a single population of taste-masked non-opioid analgesic/opioid analgesic drug-containing microparticles of the present invention in combination with excipients, rapidly dispersing microgranules, etc, or can include a combination of the taste-masked non-opioid analgesic/opioid analgesic drug-containing microparticles in combination with optionally taste-masked non-opioid analgesic drug-containing particles, or alternatively two or more populations of different optionally taste-masked non-opioid analgesic/opioid analgesic drug-containing microparticles. The ratio of the different populations of non-opioid analgesic/opioid analgesic drug-containing microparticles or non-opioid analgesic/opioid analgesic drug-containing microparticles and non-opioid analgesic drug-containing particles can be varied to provide suitable dosages of the high-dose, non-opioid analgesic and low-dose, opioid analgesic.

Alternately, the ultimate dosage form can comprise a single population of taste-masked non-opioid analgesic/opioid analgesic drug-containing microparticles of the present invention in combination with excipients, rapidly dispersing microgranules, etc, or can include a combination of the taste-masked non-opioid analgesic/opioid analgesic drug-containing microparticles in combination with modified release (e.g., taste-masked or sustained release) coated non-opioid analgesic drug-containing particles, or alternatively two or more populations of different taste-masked non-opioid analgesic/opioid analgesic drug-containing microparticles, wherein the sustained release coating of the non-opioid analgesic drug-containing microparticles comprises a water insoluble polymer optionally in combination with a water soluble or enteric polymer, for example applied prior to applying the layer of the opioid analgesic. The ratio of the different populations of non-opioid analgesic/opioid analgesic drug-containing microparticles or non-opioid analgesic/opioid analgesic drug-containing microparticles and taste-masked or sustained release coated non-opioid analgesic drug-containing particles can be varied to provide suitable dosages of the high-dose, non-opioid analgesic and low-dose opioid analgesic.

The oral dosage forms of the present invention, prepared by the methods described herein, provide in vivo plasma concentrations and release profiles which mimic RLDs. In accordance with certain embodiments, the pharmaceutical compositions of the present invention comprise microgranules or extruded/spheronized pellets comprising acetaminophen, a polymeric binder, which imparts resilient characteristics to the dried microgranules/pellets, a hydrophilic filler/diluent, and optionally a flavor, a sweetener and/or a disintegrant.

In certain embodiments, the present invention is directed to compositions comprising at least one population of non-opioid analgesic/opioid analgesic drug-containing microparticles combined with non-opioid analgesic drug-containing microparticles with drug release properties suitable for a twice- or once-daily dosing regimen, wherein one or more of the non-opioid analgesic drug-containing microparticle populations comprise non-opioid analgesic drug-containing microparticles with one or more coating layers comprising a water-insoluble polymer, an enteric polymer, or an enteric polymer in combination with a water-insoluble polymer.

In most embodiments, the taste-masked pharmaceutical compositions of the present invention exhibit the following properties:
1) acceptable taste-masking leaving no aftertaste when the composition is placed in the oral cavity for 3 minutes, more particularly for 2 minutes and in certain embodiments for 60 seconds, and in still other embodiments, until it is swallowed;
2) acceptable homogeneity of blends as per United States Pharmacopoeia requirements; and
3) rapid substantially complete release of the dose upon entry into the stomach, i.e., release of not less than 75% of the total dose in 30 min when tested for dissolution using United States Pharmacopoeia Apparatus 1 (Baskets @ 100 rpm) or Apparatus 2 (paddles @ 50 rpm in 900 mL of dissolution media at 37±0.5° C.).

An ODT prepared in accordance with certain embodiments of the present invention may exhibit the following properties:
1) exhibits acceptable uniformity of dosage forms as defined in United States Pharmacopoeia;
2) disintegrates on contact with the saliva in the oral cavity forming a smooth, easy-to-swallow suspension comprising taste-masked microparticles;
3) leaves no aftertaste after swallowing (no gritty or chalky mouthfeel);
4) provides rapid, substantially-complete release of the total dose upon entry into the stomach; or
5) the ODT when tested for dissolution using United States Pharmacopoeia Apparatus 1 (baskets @ 100 rpm) or Apparatus 2 (paddles @ 50 rpm) in 900 mL buffer releases not less than 75% of the total dose in about 30 minutes.

In another particular embodiment, the pharmaceutical composition of the present invention comprises acetaminophen as the non-opioid analgesic and hydrocodone bitartrate as the opioid analgesic. Following oral administration, acetaminophen is rapidly and almost completely absorbed from the GI tract. Peak plasma concentrations are attained within 30-60 minutes (binding to serum protein is about 25% after normal therapeutic dosages) and plasma half-life is between 1-2.5 hours in normal, healthy patients. After about 8 hours, only traces of the drug are detectable.

Pharmaceutical compositions of the present invention comprising therapeutically effective amounts of taste-masked non-opioid analgesic/opioid analgesic drug-containing microparticles are effective in treating various diseases or conditions. For example, pharmaceutical compositions of the present invention comprising therapeutically effective amounts of a non-steroidal anti-inflammatory drug such as aspirin, ibuprofen, ketoprofen, meloxicam, diclofenac potassium, etodolac, sulindac, indomthacin, celecoxib, or mixtures thereof, in combination with an opioid analgesic such as hydrocodone bitartrate, oxymorphone, buprenorphine, fentanyl, hydromorphone, or mixtures thereof (e.g. a combination of acetaminophen and hydrocodone) are effective for relief of mild to moderate pain, acute, chronic, or post-operative pain, or disabling pain of terminal conditions such as cancer.

In a particular embodiment, the pharmaceutical compositions of the present invention comprise therapeutically effective amounts of acetaminophen in combination with therapeutically effective amount of hydrocodone or salts thereof, e.g. hydrocodone bitartrate. In a specific embodiment, the pharmaceutical compositions of the present invention comprise 500 mg of acetaminophen and 5 mg of hydrocodone bitartrate, or 300 mg of acetaminophen and 100 mg of hydrocodone bitartrate. The acetaminophen/hydrocodone-containing compositions of the present invention are bioequivalent to known acetaminophen/hydrocodone compositions such as Vicodin®, Panadol®, and Xodol®. Compositions of the present invention comprising 500 mg of acetaminophen/5 mg of hydrocodone bitartrate have an acetaminophen $C_{max}$ of 80-125% of 6115 ng/mL, a hydrocodone bitartrate $C_{max}$ of 80-125% of 20.14 ng/mL, an acetaminophen AUC of 80-125% of 19920 ng·hr/mL, and a hydrocodone bitartrate AUC of 80-125% of 141 ng·hr/mL. compositions of the present invention comprising 300 mg acetaminophen/10 mg hydrocodone bitartrate have an acetaminophen $C_{max}$ of 80-125% of 3915 ng/mL, a hydrocodone bitartrate $C_{max}$ of 80-125% of 40.53 ng/mL, an acetaminophen AUC of 80-125% of 12794 ng·hr/mL, and a hydrocodone bitartrate AUC of 80-125% of 280 ng·hr/mL.

EXAMPLE 1

1.A IR Beads (Drug Load: Approximately 5% Hydrocodone Bitartrate):

Hydrocodone bitartrate (81.1 g) was slowly added to an acetone/water (1453/782) solution of hydroxypropyl cellulose (8.1 g of Nisso HPC-L-FP) and mixed well to dissolve. 60-80 mesh sugar spheres (1500 g) were coated with the drug-layering formulation in a Glatt fluid-bed coater (Glatt GPCG 3, equipped with a 7" bottom-spray Wurster insert, 7 13/16" column, 25 mm column height, 'C' air distribution plate, and 200 mesh product retention screen) under the following conditions—inlet air temperature: 70±5° C.; product temperature: 45±5° C.; atomization air pressure 2.43 bar; port size: 1.0 mm; flow rate: 2 g/min increased in steps to 15 g/min, air flow: 25% flap. Following the drug layering, a sealant coating solution of hydroxypropylcellulose (32.4 g in 457/51 acetone/water) was sprayed onto the drug layered beads for a coating weight of 2%. The dried immediate release (IR) beads were sieved through 50 and 80 mesh screens for a usable total yield of 88.4%.

1.B Taste-Masked Beads (Drug Load: Approximately 3.5% Hydrocodone Bitartrate):

IR beads (140 g) from Example 1.A, above were coated with ethylcellulose (Ethocel Standard Premium 100 from Dow Chemicals) by solvent coacervation at a coating weight of 30%. The ethylcellulose (60 g) and polyethylene (40 g Epolene C-10 from Eastman Chemicals) were dissolved/suspended in 2000 g cyclohexane at an agitation speed of 300 RPM. The tank was heated to 80° C. to dissolve the ethylcellulose, and thereafter, the tank was cooled to below 30° C. to achieve taste-masked hydrocodone bitartrate microcapsules. The microcapsules were separated by decanting, then filtered and washed with fresh cyclohexane and air dried in a fume hood.

1.C Taste-Masked Microparticles by Fluid-Bed Coating:

IR Beads (1001.3 g) prepared as described in Example 1.A, above were coated with a solution of ethylcellulose (Ethocel Standard Premium 10 cps, hereafter referred as EC-10)/Eudragit E100 (188.6 g each) plasticized with diacetylated monoglycerides (Myvacet 9-45; 30.0 g) and kosher magnesium stearate (30.0 g) dissolved in 80/20 acetone (3086 g)/water (771 g) for a coating weight of 30%. Samples were pulled during the coating process at coating weights of about 10%, 15%, 20%, and 25% and dissolution tested to evaluate the effect of coating level on dissolution and organoleptic properties. The coated beads were dried/cured at 60° C. for 10 minutes in the Glatt GPCG 3 and sieved to discard agglomerates.

1.D Standard Acetaminophen Microcapsules (PE004):

Production of industrial scale acetaminophen microcapsules using Acetaminophen Granular (Particle size: 45-80 mesh or 177-350 μm) from Covidien were coated using a method similar to that described above in Example 1.B using a 200-gallon, 500-gallon or 1000-gallon system, and using a computerized recipe for the process (e.g., quantities for the 200-gallon system at 10% coating—Acetaminophen: 94.1 kg; Ethocel 100: 10.5 kg, Epolene: 2.1 kg and Cyclohexane: 146.0 gallons or 547.5 L). Upon controlled cooling to <30° C., the microcapsule bed is subjected to vacuum filtration and rinsing with cyclohexane to wash off residual polyethylene. The microcapsules were transferred to a fluid bed dryer, subjected to a drying procedure, and dried for a period of 4-6 hrs to reduce the cyclohexane level to not more than 1000 ppm.

1.E Rapidly Dispersing Microgranules:

Rapidly dispersing microgranules comprise a sugar alcohol such as mannitol and/or a saccharide such as lactose and a disintegrant such as Crospovidone. The sugar alcohol and/or saccharide and disintegrant will typically be present in the rapidly dispersing microgranules at a ratio of from about 99:1 to about 90:10 (sugar alcohol and/or saccharide:disintegrant). For example, the rapidly dispersing microgranules used in the ODT formulations disclosed in the various examples in accordance with the present invention were produced by granulating 95 parts of D-mannitol with an average particle size of about 15 μm, and 5 parts of crospovidone (Crospovidone XL-10) in a high shear mixer (e.g., GMX 600 from Vector Corporation) with water as the granulating fluid, drying the wet mass in a fluid bed dryer (e.g., Glatt GPCG 200 or Fluid Air FA0300), and sieving/milling to obtain granules with an average particle size of less than 400 μm. Alternately, the wet milled granules are dried in a tray drying oven for a loss on drying value of less than 1% by weight.

1.F Hydrocodone Bitartrate/Acetaminophen ODTs, 5 mg/500 mg:

Beads (172.4 g) prepared as described in Example 1.B (30% coating weight), above; standard acetaminophen microcapsules (PE004, 531.9 g) produced in Example 1D, above, and rapidly dispersing microgranules (803.4 g) from Example 1E above, were blended with a pre-blend comprising crospovidone (XL-10, 80.0 g), sucralose (5.6 g), and strawberry flavor (6.7 g) before compressing into 5 mg/500 mg hydrocodone bitartrate/acetaminophen orally disintegrating tablets (19 mm in diameter) weighing approximately 1600 mg using a Carver tablet press at a compression force of 1 metric ton.

EXAMPLE 2

2.A Hydrocodone Bitartrate/Acetaminophen Microparticles (Drug Load: 3%):

Hydrocodone bitartrate (47.5 g) was slowly added to a 50/50 acetone/water (each 452 g) solution of hydroxypropylcellulose (5.3 g of Nisso HPC-L-FP) and mixed well to dissolve. Acetaminophen microcapsules (PE004) from Example 1.D with a 6% EC-100 coating (1500.0 g) were coated with the drug-layering formulation in a Glatt fluid-bed coater Glatt GPCG 3. Following drug layering, a sealant coating solution of hydroxypropylcellulose (31.7 g in 447/50 acetone/water) was sprayed onto the drug layered beads at a coating weight 2%. The dried IR beads were sieved through 35 and 80 mesh screens for a usable total yield of 99.0%.

2.B Taste-Masked Hydrocodone Bitartrate/Acetaminophen Microparticles:

IR particles (1100.0 g) prepared as described in Example 2.A, above were coated with a solution of ethylcellulose (EC-10; 43%)/Eudragit E100 (43%) plasticized with diacetylated monoglycerides (Myvacet 9-45 at 7%) and kosher magnesium stearate (7%) dissolved in 80/20 acetone (3294 g)/water (848 g) for a 30% weight gain. Samples were pulled during the coating process at coating weights of about 5%, 10%, 15%, 20%, and 25% and dissolution tested to evaluate the effect of coating level on dissolution as well as organoleptic properties. The coated beads were dried at the same temperature settings in the Glatt GPCG 3 and sieved to discard agglomerates for a total useable yield of 98.9%.

2.C Hydrocodone Bitartrate/Acetaminophen ODTs, 10 mg/300 mg:

20% EC-10/E100 coated (10.01% of hydrocodone bitartrate/Acetaminophen beads at 15% hydrocodone bitartrate load) from Example 2.B, above; standard acetaminophen microcapsules (PE004, 35.46%) from Example 1.D, above, and rapidly dispersing microgranules (48.76%) from Example 1.E above, were blended with a pre-blend comprising crospovidone (XL-10 at 5.0%), sucralose (0.35%), and strawberry flavor (0.42%) before compressing into 10 mg/300 mg hydrocodone bitartrate/acetaminophen orally disintegrating tablets (15 mm in diameter) weighing approximately 900 mg using a Carver tablet press at a compression force of 1 metric ton.

2.D Hydrocodone Bitartrate/Acetaminophen ODTs, 5 mg/500 mg:

30% coated beads (10.78%) from Example 2.B, above, standard acetaminophen microcapsules (PE004, 33.24%) from Example 1.D, above, and rapidly dispersing microgranules (37.71%) from Example 1.E above, were blended with a pre-blend comprising microcrystalline cellulose (Avicel PH101 at 12.5%), crospovidone (XL-10 at 5.0%), sucralose (0.35%), and strawberry flavor (0.42%) before compressing into 5 mg/500 mg hydrocodone bitartrate/acetaminophen orally disintegrating tablets (17 mm in diameter) weighing approximately 1600 mg using a rotary Hata tablet press equipped with an external lubrication system (Matsui Ex-Lub System) to lubricate the die/punch surfaces by spraying magnesium stearate prior to each compression.

EXAMPLE 3

3.A Taste-Masked Acetaminophen Microparticles:

Acetaminophen (Granular grade from Covidien (A100); 2000.0 g) was coated in a Glatt GPCG 3 (7" bottom spray Wurster insert and nozzle with 1.00 mm port size) with a solution of ethylcellulose (10 cps; 114.3 g)/Eudragit E100 (100.0 g) plasticized with polyethylene glycol (PEG 400; 42.9 g) and kosher magnesium stearate (28.6 g) homogeneously suspended in acetone (1359.5 g)/isopropyl alcohol (672.7 g)/water (770.8 g) for a 12.5% weight gain. The dried particles were sieved with 35 and 80 mesh screens to discard agglomerates/fines (useable yield: 93.6%).

3.B Low Potency Hydrocodone Bitartrate/Acetaminophen:

Hydrocodone bitartrate was layered onto acetaminophen (Granular A100) by spraying the drug-layering formulation (see Table 1—Low Potency for compositions) in a Glatt GPCG 3 fluid-bed coater. Following the drug layering, the sealant coating solution was sprayed onto the drug layered particles at a coating weight of 2%, followed by a taste-masking coating with EC-10/E100/PEG 400/Mg stearate at a ratio of 40/35/15/10 at a coating weight of 22% using the method disclosed in Example 3.A above.

3.C High Potency Hydrocodone Bitartrate/Acetaminophen:

Hydrocodone bitartrate was layered onto acetaminophen (Granular A100) by spraying the drug-layering formulation (see Table 1—High Potency for compositions) in a Glatt GPCG 3 fluid-bed coater. Following the drug layering, the sealant coating solution was sprayed onto the drug layered particles at a coating weight of 2%, followed by a taste-masking coating with EC-10/E100/PEG 400/Mg stearate at a ratio of 40/35/15/10 at a coating weight of 27%.

TABLE 1

Taste-Masked Low Potency (PE382)/High Potency ((PE384) Hydrocodone Bitartrate/Acetaminophen (A100)

| Ingredients Taste-masked Hydrocodone/Acetaminophen - PE382 (LP)/PE384 (HP) or Acetaminophen PE380 | Percent | | | Quantity Required.(g) | |
|---|---|---|---|---|---|
| | Low Potency | High Potency | PE380 | Low Potency | High Potency |
| LP/HP HCB on Acetaminophen (A100) | | | | | |
| Acetaminophen Granular (A100) | 96.06 | 90.22 | | 2500.0 | 2000.0 |
| Hydrocodone Bitartrate, NF | 1.75 | 7.00 | | 45.5 | 155.2 |
| Hydroxypropylcellulose, NF (Klucel LF) | 0.196 | 0.78 | | 5.1 | 17.2 |
| Acetone, NF* | | | | 432.7 | 1474.1 |
| Purified Water, USP | | | | 432.7 | 1474.1 |
| Hydroxypropylcellulose (Klucel ® LF) | 1.70 | 1.70 | | 44.2 | 37.7 |
| Magnesium Stearate NF | 0.30 | 0.30 | | 7.8 | 6.7 |
| Acetone NF* | | | | 611.6 | 520.9 |
| Purified Water USP * | | | | 203.9 | 173.6 |
| Total | 100.0 | 100.0 | | 2602.6 | 2216.8 |
| Taste-masking Coating - (5% Solids) | | | | | |
| LP/HP Hydrocodone-layered Acetaminophen | 78.00 | 73.00 | | 2000.0 | 1500.0 |
| Acetaminophen Granular (A100) | | | 2000.0 | | |
| Ethylcellulose NF (Ethocel ® Standard 10 Premium) | 8.80 | 10.80 | 114.3 | 225.6 | 221.9 |
| Aminoalkyl Methacrylate Copolymer E (Eudragit ® E 100) | 7.70 | 9.48 | 100.0 | 197.4 | 194.2 |
| Polyethylene Glycol (Carbowax ® 400) | 3.30 | 4.05 | 42.9 | 84.6 | 83.2 |
| Magnesium Stearate NF | 2.20 | 2.70 | 28.6 | 56.4 | 55.5 |
| Acetone NF* | Traces | Traces | 1359.5 | 2684.1 | 2639.8 |
| Isopropyl Alcohol USP* | Traces | Traces | 672.7 | 1328.2 | 1306.3 |
| Purified Water USP* | Traces | Traces | 770.8 | 1521.9 | 1496.8 |
| Total | 100.0 | 100.0 | 2285.8 | 2564.0 | 2054.8 |

3.D Hydrocodone Bitartrate/Acetaminophen ODTs, 5 mg/500 mg:

12.5% coated acetaminophen from Example 3A, above, 22% coated hydrocodone/acetaminophen from Example 3B, above, rapidly dispersing microgranules from Example 1.E above, were blended with a pre-blend comprising microcrystalline cellulose (Avicel PH 101), (Parteck M200), crospovidone, sucralose, and strawberry flavor before compressing into 5 mg/500 mg hydrocodone bitartrate/acetaminophen orally disintegrating tablets (17 mm in diameter) weighing approximately 1600 mg using a using a rotary Hata tablet press equipped with an external lubrication system (Matsui Ex-Lub System) to lubricate the die/punch surfaces prior to each compression at a compression force of 18 to 24 kN.

3.E Hydrocodone Bitartrate/Acetaminophen ODTs, 10 mg/300 mg:

12.5% coated acetaminophen from Example 3.A, above, 27% coated hydrocodone/acetaminophen from Example 3.C, above, and rapidly dispersing microgranules from Example 1.E above, were blended with a pre-blend comprising microcrystalline cellulose (Avicel PH101), mannitol (Parteck M200), crospovidone, sucralose, and strawberry flavor before compressing into 5 mg/500 mg hydrocodone bitartrate/acetaminophen orally disintegrating tablets (17 mm in diameter) weighing approximately 1000 mg using a using a rotary Hata tablet press equipped with an external lubrication system (Matsui Ex-Lub System) to lubricate the die/punch surfaces prior to each compression at a compression force of 10 to 15 kN (see Table 2 for details).

TABLE 2

Hydrocodone Bitartrate/Acetaminophen ODTs, 5 mg/500 mg & 10 mg/300 mg

|  |  | Hydrocodone/Acetaminophen ODTs | | | |
|---|---|---|---|---|---|
|  |  | PF401 (5 mg/500 mg) | | PF402 (10 mg/300 mg) | |
| Item | Ingredient | %/tablet | g/Batch | %/tablet | g/Batch |
| 1 | Low-potency Taste-masked Hydrocodone Bitartrate/Acetaminophen (PE382) | 22.89 | 572.25 |  |  |
| 2 | High-potency Taste-masked Hydrocodone/Acetaminophen (PE384) |  |  | 15.66 | 391.5 |
| 3 | Acetaminophen Microcapsules (PE380) | 16.11 | 402.75 | 15.60 | 390.0 |
| 4 | Rapidly Dispersing Granules | 40.15 | 1003.75 | 49.70 | 1242.5 |
| 5 | Mannitol, USP (Parteck® M200) | 4.25 | 106.25 | 5.00 | 125.0 |
| 6 | Microcrystalline Cellulose, NF | 10.00 | 250.0 | 10.00 | 250.0 |
| 7 | Crospovidone, NF (XL-10) | 5.25 | 131.25 | 5.26 | 131.3 |
| 8 | Sucralose, NF | 0.35 | 8.75 | 0.35 | 8.8 |
| 9 | Artificial Strawberry Flavor | 1.00 | 25.00 | 1.00 | 25.0 |
| 10 | Magnesium Stearate | Traces | Traces | Traces | Traces |
|  | Total | 100.0 | 2500.0 | 100.0 | 2500.0 |
|  | Tablet Weight (mg) | 1600.0 |  | 1250.0 |  |

EXAMPLE 4

4.A Pilot PK Trial Supplies:

Two tablet strengths of hydrocodone bitartrate/acetaminophen ODTs—5 mg/500 mg and 10 mg/300 mg, and three different taste-masked particle compositions were used between these two strengths: 1) acetaminophen crystals (A100—standard particle size, i.e., 177-350 μm) with a taste-masking coating composition used in both ODT formulations; 2) acetaminophen crystals (standard particle size) with a 1.75% w/w drug layer of hydrocodone bitartrate and a subsequent taste-masking coating, used in the 5 mg/500 mg strength; and 3) acetaminophen crystals (standard particle size) with a 7% w/w drug layer of hydrocodone bitartrate and a subsequent taste-masking coating, used in the 10 mg/300 mg strength. The taste-masking coating was compositionally the same for all particles, but the amount of coating on a w/w basis varies from 12.5% on acetaminophen (PE380), 22% on 1.75% hydrocodone bitartrate/acetaminophen (PE382) used in 5 mg/500 mg ODTs (PF401) to 27% on 7% hydrocodone bitartrate/acetaminophen (PE384) used in 10 mg/300 mg ODTs (PF402). The compression blend is compressed into hydrocodone bitartrate/acetaminophen ODTs using an Elizabeth Hata tablet press equipped with a Matsui Ex-Lub lubricating system that uses magnesium stearate as an external lubricant. Each of the dosages has a unique blend and was prepared using different tableting parameters (see Table 3 below for details). These ODT batches were prepared as described in Examples 3.A to 3.E (see Tables 1 and 2 for compositions. The intermediate and finished products were tested using qualified analytical test methods and used in the pilot PK study in healthy volunteers.

TABLE 3

Tableting Parameters for Hydrocodone Bitartrate/Acetaminophen ODTs:

| Parameter | 5 mg/500 mg ODT | 10 mg/300 mg ODT |
|---|---|---|
| Tooling - round, flat face, radius edge | 17 mm | 15 mm |
| Target tablet weight (mg) | 1600 | 1250 |
| Lower target tablet weight × 0.985 (mg) | 1576 | 1231 |

TABLE 3-continued

Tableting Parameters for Hydrocodone Bitartrate/Acetaminophen ODTs:

| Parameter | 5 mg/500 mg ODT | 10 mg/300 mg ODT |
|---|---|---|
| Target tablet weight × 1.015 (mg) | 1624 | 1269 |
| Turn table speed with range (rpm) | 15 (10-20) | 15 (10-20) |
| Fill depth (mm) | 10.94-10.98 | 5.11 |
| Main position (mm) | 10.6-11.1 | 4.44 |
| Pre. Position (mm) | 6.2-6.4 | 4.61 |
| Scale on the feed shoe | 2 (0-4) | 2 (0-4) |
| Tablet Weight (mg) | 1597 | 1248.6 |
| Hardness with range (n) | 6.80 | 6.92-6.95 |
| Thickness with range (mm) | 47-49 | 40-42 |
| Friability with range (%) | 0.25-0.31 | 0.24-0.31 |

Figure 2:
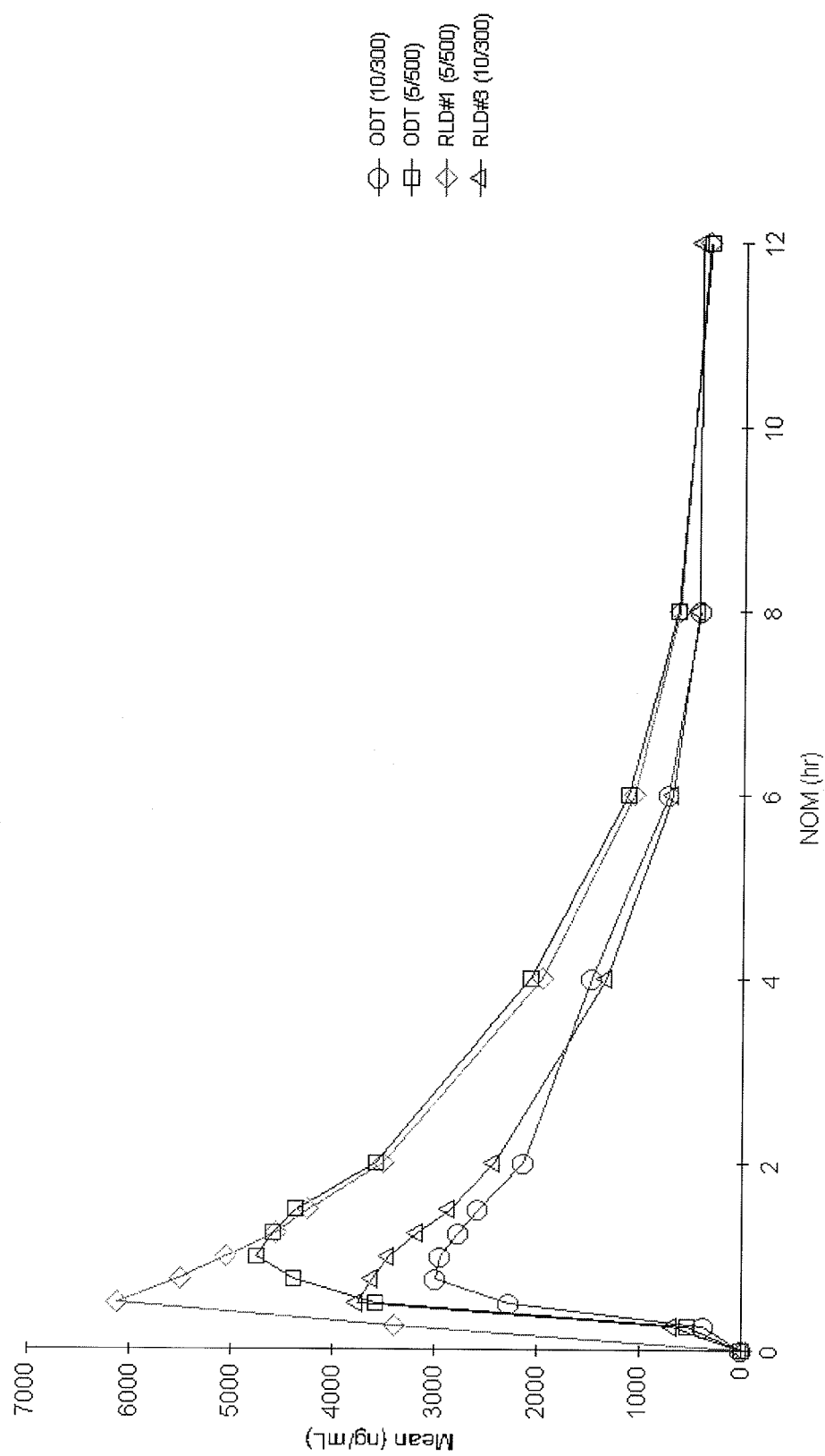
FIG. 2 illustrates the plasma concentration—time profiles for acetaminophen of hydrocodone bitartrate/acetaminophen tablets observed in the pilot PK (pharmacokinetics) study.
Figure 3:
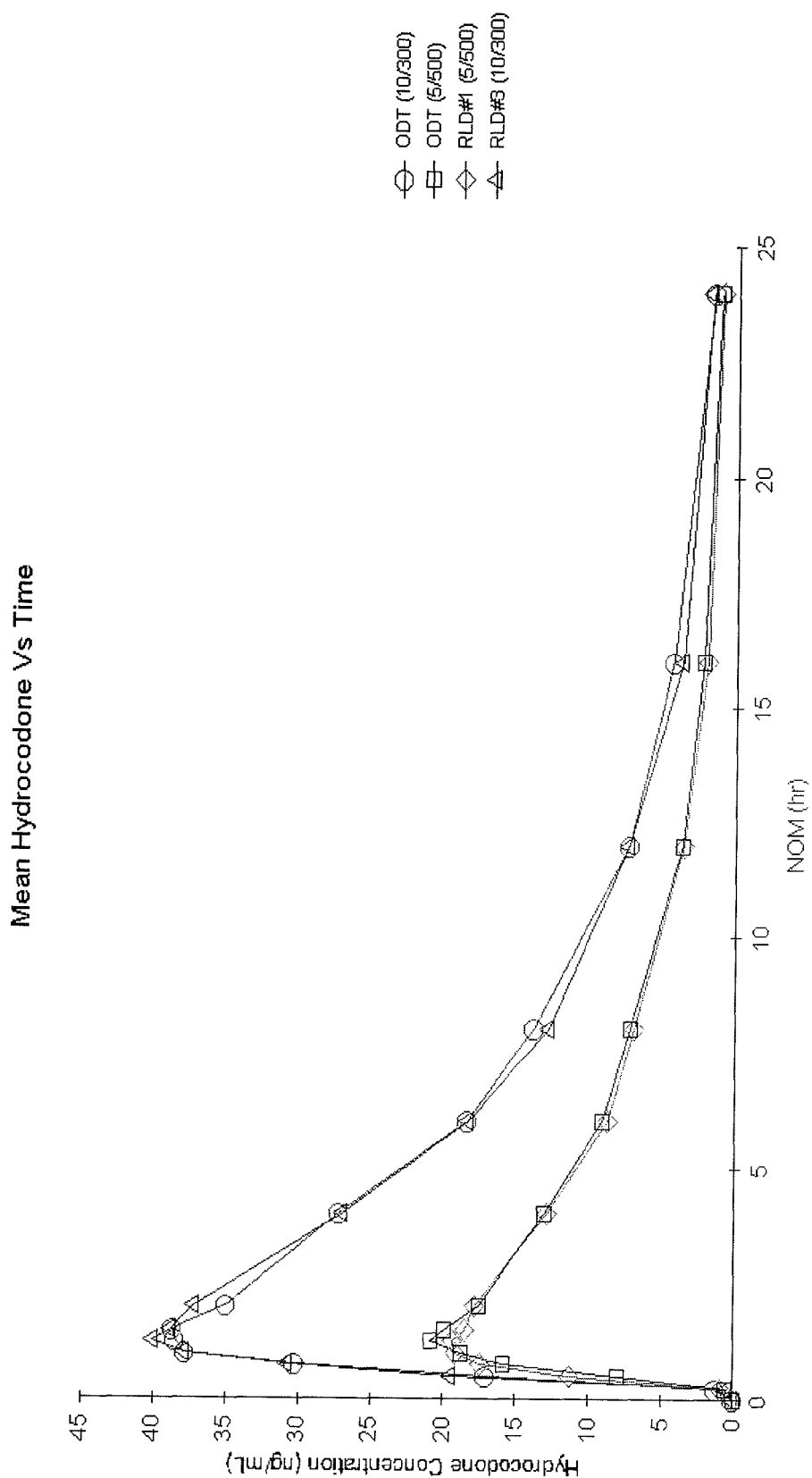
FIG. 3 illustrates the plasma concentration—time profiles for hydrocodone bitartrate of hydrocodone bitartrate/acetaminophen tablets observed in the pilot PK (pharmacokinetics) study.

4.B Pilot PK (Pharmacokinetics) Study:

Hydrocodone bitartrate/acetaminophen ODTs, 5 mg/500 mg and 10 mg/300 mg dosages were tested in a 4-arm pilot PK (pharmacokinetics) study involving 16 healthy subjects per aim in comparison to the corresponding RLDs, Abbott's VICODIN® 5 mg/500 mg, Mikart's Xodol®, 10 mg/300 mg. Acetaminophen and hydrocodone bitartrate plasma concentration vs. time profiles for these ODTs are shown in FIGS. 2 and 3.

TABLE 4

PK Parameters for Hydrocodone/Acetaminophen ODTs

| Test# ODT | RLD IR | Active | Test ODT | RLD | Ratio Test/RLD | Min-Max |
|---|---|---|---|---|---|---|
| | | | $C_{max}$ (ng/mL) | | | |
| 5/500 mg | Vicodin | Acetaminophen | 5013.86 | 6115.49 | 81.99 | 67.79-99.15 |
| | | | $AUC_{0 \to inf}$ (ng · hr/mL) | | | |
| | | | 19205.98 | 19917.76 | 96.43 | 79.17-117.4 |
| | | | $C_{max}$ (ng/mL) | | | |
| 10/300 mg | Xodol | Acetaminophen | 3159.55 | 3914.16 | 80.72 | 67.80-96.10 |
| | | | $AUC_{0 \to inf}$ (ng · hr/mL) | | | |
| | | | 12196.49 | 12794.85 | 95.32 | 79.55-114.2 |
| | | | $C_{max}$ (ng/mL) | | | |
| 5/500 mg | Vicodin | Hydrocodone | 19.708 | 20.139 | 97.86 | 90.44-105.9 |
| | | | $AUC_{0 \to inf}$ (ng · hr/mL) | | | |
| | | | 141.36 | 141.40 | 99.97 | 93.56-106.8 |
| | | | $C_{max}$ (ng/mL) | | | |
| 10/300 mg | Xodol | Hydrocodone | 38.719 | 40.530 | 95.53 | 88.87-102.7 |
| | | | $AUC_{0 \to inf}$ (ng · hr/mL) | | | |
| | | | 286.33 | 279.06 | 102.6 | 96.25-109.4 |

Figure 4:
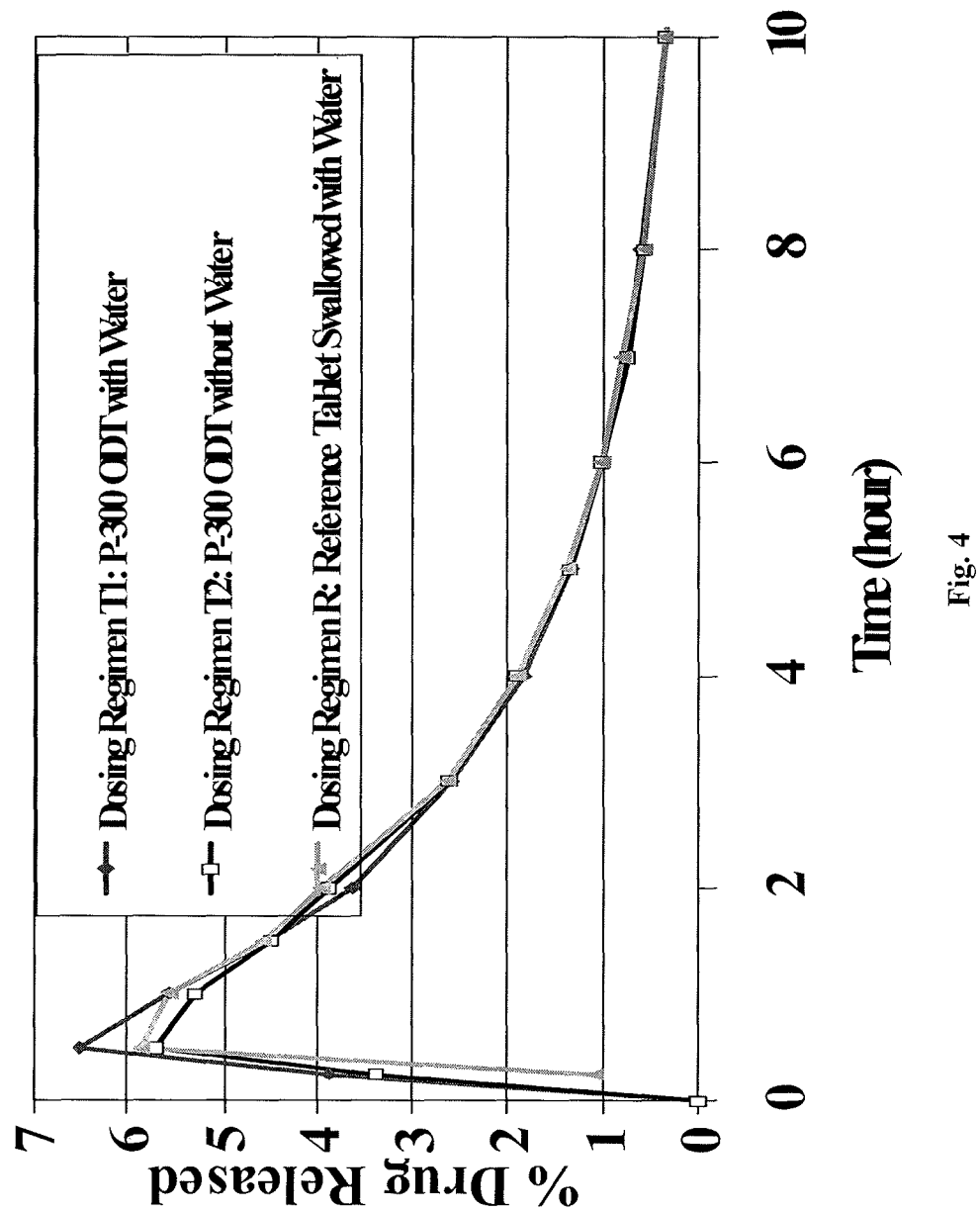
FIG. 4 illustrates the plasma concentration—time profiles for acetaminophen of Acetaminophen ODTs versus Panadol® observed in the pilot PK (pharmacokinetics) study.

FIG. 4 shows the plasma concentration-time profiles for acetaminophen observed in another 3-arm pilot PK study involving 24 healthy subjects per arm wherein Acetaminophen ODT, 500 mg with or without water was administered to fasted healthy volunteers in comparison to the corresponding RLD, GSK's Panadol® 500 mg. Acetaminophen of semi-fine grade (A137) with a smaller particle size distribution of 53-177 μm were taste-masked by solvent coacervation with Ethocel Standard Premium 100 cps for a coating weight of 10-12%. To produce orally disintegrating tablets, these microcapsules were blended with rapidly dispersing microgranules (PE378 prepared from mannitol 25/crospovidone at 95/5 as disclosed in Example 1.E, above), crospovidone, microcrystalline cellulose, aspartame (sweetener) and strawberry flavor in a V-blender and then compressed on a rotary tablet press equipped with an external lubrication system. These tablets (see Table 5 for compositions) released not less than 85% in 15 min when tested using the USP apparatus 2 (paddles@ 75 rpm in pH 5.8 buffer (see Table 6 for dissolution data).

TABLE 5

Compositions of Acetaminophen ODTs

| Ingredients | % per tablet | ODT (mg/tablet) 250 mg | ODT (mg/tablet) 500 mg | Quantity (kg)/Batch 250 mg/500 mg |
|---|---|---|---|---|
| Taste-masked (10-12%) Acetaminophen (A137) | 39.68 | 277.8 | 555.5 | 63.5 |
| Rapidly Dispersing Granules (PE375) | 42.12 | 294.8 | 589.7 | 67.4 |
| Microcrystalline Cellulose (Avicel PH101) | 10.00 | 70.0 | 140.0 | 8.0 |
| Crospovidone NF (XL-10) | 5.00 | 35.0 | 70.0 | 16.0 |
| Sucralose NF | 1.60 | 11.2 | 22.4 | 2.56 |
| Strawberry Flavor | 1.60 | 11.2 | 22.4 | 2.56 |
| Total | 100.0 | 700.0 | 1400.0 | 160.0 |

The PK parameters for Acetaminophen ODTs in comparison to Panadol® are given below:

Regimen T1: Acetaminophen (P-300) ODT with water
Regimen T2: Acetaminophen (P-300) ODT without water
Regimen 3: Reference tablet (Panadol®) swallowed with water

| PK Parameter | Test 1 (ODT) With water | Test 2 (ODT) W/O water | 90% Confidence Interval Test T1 vs. RLD | 90% Confidence Interval Test T2 vs. RLD |
|---|---|---|---|---|
| $C_{max}$ (ng/mL) | 7.240 | 7.635 | 90.94-110.25 | 94.04-114.01 |
| $AUC_{0-t}$ (ng · hr/mL) | 21.44 | 21.00 | 99.61-106.19 | 98.06-104.53 |
| $AUC_{0-INF}$ (ng · hr/mL) | 22.43 | 21.69 | 99.41-106.33 | 96.82-103.57 |

The above results confirm that the test product, Acetaminophen ODT, 500 mg when administered with and without water is bioequivalent to the reference product, Panadol®, 500 mg swallowed with water. Multi-speed (50, 75 and 100 rpm) and multi-pH in vitro dissolution (water, pH 1.2, 4.5, 5.8, 6.8) data were generated on batches of 5 mg/500 mg and 10 mg/300 mg ODT tablets of Example 3 and 4 and 250 mg and 500 mg ODT tablets of Example 4, and a comparative data set is presented in Table 6. Since different grades of the drug substance such as Acetaminophen Granular and Acetaminophen Semi-fine were used to manufacture batches of 5 mg/500 mg-10 mg/300 mg ODT tablets and 250 mg-500 mg ODT tablets, respectively, the particle size distributions of several lots of the drug substance and the corresponding batches of microcapsules were determined. Table 7 shows the mean particle size distribution data.

TABLE 6

Dissolution Data for Hydrocodone/Acetaminophen IR
Tablets and ODTs and Acetaminophen ODT

| Time (min) | PF401EA 5 mg/500 mg | PF402EA 10 mg/300 mg | Vicodin* 5/500 mg | Xodol 10/300 mg | PF407EA 250 mg | PF408EA 500 mg |
|---|---|---|---|---|---|---|
| 0 | 0 | 0 | 0 | 0 | 0 | 0 |
| 5 | 23 | 28 | 49 | 40 | | |
| 10 | 53 | 60 | 65 | | 87 | 75 |
| 15 | 75 | 87 | 71 | 84 | 95 | 88 |
| 30 | 101 | 103 | 76 | 93 | | |

*→ Vicodin is released by USP test 2 which is 0.1N HCl media

TABLE 7

Particle Size Distributions of Acetaminophen
Drug Substance and Microcapsules

| | Acetaminophen Drug Substance | | Microcapsules | |
|---|---|---|---|---|
| Grade | % Particles Retained on | Coating | % Particles Retained | % Assay (STD) |
| Granular | | | | |
| (Mean of multiple batches) | >80% <425-180 μm> | 6% (500/1000 gallon) | 95% <425-180 μm> | 93 ± 1.37 |
| Semi-fine | | | | |
| Mean of multiple batches | 90% <150-53 μm> | 12% (5-gallon) | 87% <250-74 μm> | 87.9 |
| A13709532 | 89.5% <150-53 μm> | 12% (500-gallon) | 90% <250-74 μm> | 86.8 |
| A13709533 | 86.2% <150-53 μm> | 10% (500-gallon) | 89.5% <250-74 mesh | 89.7 |

Acetaminophen/Hydrocodone ODT tablets (5 mg/500 mg or 10 mg/300 mg ODTs) contain two of three types of microencapsulated acetaminophen drug particles—granular grade acetaminophen and granular grade acetaminophen drug particles layered with hydrocodone at a low or high drug load, all taste-masked with a coating of ethylcellulose/Eudragit EPO. To improve the dissolution and bioequivalence to the RLDs and to improve the stability of hydrocodone when directly layered onto acetaminophen particles, it was decided to use the drug substance with a smaller particle size distribution (e.g., Acetaminophen Semi-fine) in the tablet formulation to manufacture "smaller acetaminophen microcapsules".

During the evaluation of different taste-masking coatings applied on microparticles comprising hydrocodone bitartrate for their ability to impart acceptable organoleptic properties, it was discovered that a coating comprising a sweetener in combination with a seal coating layer comprising hydroxypropylcellulose (Klucel LF) was effective in masking the bitter taste of hydrocodone bitartrate.

EXAMPLE 5

5.A Taste-Masked Acetaminophen Microparticles (6%):

Acetaminophen (Semi-fine grade from Covidien with a particle size of 80-270 mesh or 53-177 μm (A137); 1800.0 g) was taste-masked by solvent coacervation in a 5-gallon system. The 5-gallon system filled with 10,000 g of cyclohexane was charged with ethylcellulose (Ethocel Standard Premium 100 from Dow Chemicals; 114.9 g), polyethylene (Epolene C-10; 50 g), and the drug. The system was subjected to a controlled heating cycle to achieve a temperature of 80° C. to dissolve ethylcellulose while agitating the contents at a speed of 300 RPM. Thereafter the system was subjected to a computer controlled cooling cycle to <28° C. in not less than 45 min to encapsulate the drug crystals with a smooth coating at a coating weight of 6%, and avoiding formation of agglomerates. The microcapsules were separated by decanting, washed with fresh cyclohexane, and dried in a fume hood. The microcapsules with a size less than 35 mesh were collected for taste-masking (useable yield: 98.0%).

5.B Taste-Masked Hydrocodone Bitartrate/Acetaminophen Microcapsules:

Hydrocodone bitartrate (57.4 g), acetaminophen (semi-finer grade A137; 1742.6 g), ethylcellulose (156.5 g), polyethylene (50.0 g) were suspended in cyclohexane in the 5 gallon system, and HCB/Acetaminophen microencapsulated particles at an EC-100 coating of 8% by weight were produced following the procedure of Example 5.A. Hydrocodone bitartrate/Acetaminophen microencapsulated particles (1518.8 g) were sealant coating with Klucel LF (288.6 g)/magnesium stearate (15.2 g) and further provided with a second taste-masking membrane comprising ethylcellulose (EC-10)/Eudragit E100/Myvacet/magnesium stearate at a ratio of 286.6/253.5/31.8/35.7 in a Glatt GPCG 3 for a coating weight of 25% as described in Example 3.

5.C Taste-Masked Hydrocodone Bitartrate/Acetaminophen Microcapsules:

Hydrocodone bitartrate (60.0 g and 6.7 g of Klucel LF) was layered onto acetaminophen microcapsules (Semi-fine A137 with an EC-100 coating weight of 6% from Example 5.A; 1205.3 g) in the Glatt GPCG 3 for a coating weight of 8% as described in Example 3. Following the drug layering, a sealant coating with Klucel LF (28.0 g) was sprayed onto the hydrocodone-layered particles, followed by a taste-masking coating with EC-10/E100/PEG 400/Myvacet 9-45 at a ratio of 40/35/15/10 for a coating weight of 35%.

5.D Hydrocodone Bitartrate/Acetaminophen ODTs:

A compression blend comprising taste-masked Hydrocodone/Acetaminophen microparticles from Example 5.B, above, or taste-masked Hydrocodone/Acetaminophen microparticles from Example 5.C, above was combined with the rapidly dispersing microgranules from 1.E, above, and a pre-blend comprising microcrystalline cellulose, crospovidone, sucralose, and strawberry flavor, and compressed into hydrocodone bitartrate/acetaminophen ODTs, 5 mg/500 mg and 10 mg/300 mg (see Table 8 for compositions) using an Elizabeth Hata tablet press equipped with a Matsui Ex-Lub lubricating system that uses magnesium stearate as an external lubricant.

TABLE 8

Compositions of Acetaminophen ODTs

| Ingredients (mg/tablet) | ODTs, 5 mg/ 500 mg | | ODTs 10 mg/ 300 mg | |
|---|---|---|---|---|
| | 1300-086 | 1300-088 | 1300-085 | 1300-087 |
| Taste-masked Hydrocodone/ Acetaminophen (Example 5.B) | 287.4 | | 344.8 | |
| Taste-masked Hydrocodone/ Acetaminophen (Example 5.C) | | 172.4 | | 344.8 |
| Acetaminophen Microcapsules (PE378) | 378.4 | 445.4 | 123.3 | 123.3 |
| Rapidly Dispersing Granules | 496.9 | 544.9 | 445.5 | 445.5 |
| Microcrystalline Cellulose (Avicel PH101) | 140.0 | 140.0 | 110.0 | 110.0 |
| Crospovidone NF (XL-10) | 70.0 | 70.0 | 55.0 | 55.0 |
| Sucralose NF | 4.9 | 4.9 | 3.85 | 3.85 |
| Strawberry Flavor | 22.4 | 22.4 | 17.6 | 17.6 |
| Total | 1400.0 | 1400.0 | 1100.0 | 1100.0 |

Table 9 presents the dissolution profiles of hydrocodone bitartrate and acetaminophen from ODTs. A slightly thicker coating on acetaminophen drug particles by coacervation (EC-100) or a thicker fluid-bed coating (EC-10/E100) appeared to have little impact on drug dissolution rates.

TABLE 9

Dissolution Data for Hydrocodone Bitartrate/Acetaminophen ODTS

| | Hydrocodone Bitartrate Released (%) | | | | Acetaminophen Released (%) | | | |
|---|---|---|---|---|---|---|---|---|
| | ODT (10 mg/300 mg) | | ODT (5 mg/500 mg) | | ODT (10 mg/300 mg) | | ODT (5 mg/500 mg) | |
| Time (min) | 1300-085 | 1300-087 | 1300-086 | 1300-088 | 1300-085 | 1300-087 | 1300-086 | 1300-088 |
| 0 | 0 | 0 | 0 | 0 | 0 | 0 | 0 | 0 |
| 5 | 90 | 101 | 87 | 98 | 54 | 49 | 47 | 51 |
| 10 | 94 | 104 | 91 | 101 | 91 | 80 | 81 | 81 |
| 15 | 94 | 104 | 92 | 101 | 102 | 95 | 93 | 92 |
| 30 | 95 | 104 | 93 | 102 | 105 | 103 | 98 | 98 |

EXAMPLE 6

6.A Microencapsulation of Acetaminophen:

A 200-gallon solvent coacervation system (146 kg) was charged with acetaminophen (Semifine grade A137; 75.5 kg), Ethylcellulose (EC-100; 4.8 kg), Epolene; 2.1 kg) and the acetaminophen was taste-masked by solvent coacervation in a 200-gallon system while agitating at 80±5 RPM. A computer controlled "heat to 80° C.- and hold" cycle was used to achieve a temperature of 80° C. to dissolve the ethylcellulose in the coacervation system. Thereafter the system was subjected to a cooling cycle to <28° in not less than 45 min to encapsulate the acetaminophen crystals with a smooth coating at 6% by weight, and avoiding the formation of agglomerates. The microcapsules were vacuum-filtered, washed with cyclohexane, and dried in a fluid bed dryer using a 3-step temperature (e.g., 25° C., 35° C., 99° C.) for 4 to 6 hrs to achieve a residual cyclohexane level of less than 1000 ppm. The microcapsules were sieved through a US 35 mesh sieve. Following the same procedure, several batches of microcapsules (batch size: 80 kg) were prepared at a coating weight of 6% in the 200 gallon system.

6.B Taste-Masked Hydrocodone/Acetaminophen Microparticles:

Hydrocodone bitartrate (see Table 10 for compositions and batch quantities) was layered onto acetaminophen microcapsules (6% EC-100 coating; 3375.0 g) from Example 6.A, above by spraying the drug-layering formulation comprising hydroxypropylcellulose (10% solids) in a Glatt GPCG 5 (9" Wurster, 25 mm partition gap, 200 mesh product retention screen, 1.0 mm nozzle tip diameter, 'C' bottom air distribution plate; product temperature: 37±3° C.; inlet air volume: 40-45 CFM; spray rate: 8-24 ml/min) for a hydrocodone bitartrate load of 9.0%. A sealant coating solution of hydroxypropyl (5.0% or 73.68 g dissolved in 50/50 acetone/water at 10% solids) was sprayed onto the drug-layered particles (1400 g) in a Glatt GPCG 3, for a coating weight of 5%, followed by a taste-masking coating with sucralose (5.0%) dissolved in an aqueous solution of hydroxypropylcellulose (1.24%; at a ratio of 80/20 sucralose/HPC) using the following process conditions: Inlet temperature: 57±2° C.; product temperature: 37±2° C.; spray rate: 8 mL/min; inlet air volume: 6 CFM.

6.C Taste-Masked Hydrocodone/Acetaminophen Microparticles:

Hydrocodone bitartrate (see Table 10 for compositions and batch quantities) was layered onto acetaminophen microcapsules (6% EC-100 coating; 3733.3 g) from Example 6.A, above by spraying a drug-layering formulation comprising hydroxypropylcellulose (10% solids) in a Glatt GPCG 5 as described in Example 6.B, above. Following the coating, the microparticles were sealant coated with hydroxypropylcellulose at 5% in the same unit, dried for 5 minutes to reduce residual moisture and sieved through 30 and 80 mesh sieves to discard over sized particles and fines.

TABLE 10

5.0% Sucralose/5.0% HPC/Hydrocodone Bitartrate/Acetaminophen Microparticles

| Ingredients 5.0% Sucralose/5.0% HPC Coated Hydrocodone/Acetaminophen Microcapsules | Percent | | Quantity Required (g) | |
|---|---|---|---|---|
| | Formula A | Formula B | Formula A | Formula B |
| Drug Layering - (10% solids) | | | | |
| Microcaps APAP (A137) (6% Coating) | 80.16 | 84.24 | 3375.0 | 3733.3 |
| Hydrocodone Bitartrate, NF | 8.02 | 5.41 | 337.5 | 240.0 |
| Hydroxypropyl Cellulose, NF (Klucel LF) | 0.89 | 0.60 | 37.5 | 26.7 |
| Acetone, NF | Traces | Traces | 2400.0 | |
| Purified Water, USP | Traces | Traces | 3375.0 | 2400.0 |
| HPC Sealant Coat - (6% solids) | | | | |
| Hydrocodone/Acetaminophen Microcapsules | 89.07 | 90.25 | 1400.0 | 4000.0 |
| Hydroxypropyl Cellulose, NF (Klucel LF) | 4.69 | 4.75 | 73.68 | 210.5 |
| Acetone, NF | Traces | Traces | 614.0 | 1649.1 |
| Purified Water, USP | Traces | Traces | 614.0 | 1649.1 |
| Sucralose Coat (15% solids) | | | | |
| HPC Coated Hydrocodone/Acetaminophen | 93.76 | 95.00 | 1300.0 | 3400.0 |
| Sucralose, NF | 5.00 | 5.00 | 69.33 | 179.0 |
| Hydroxypropyl Cellulose, NF (Klucel LF) | 1.24 | | 17.19 | |
| Purified Water, USP | Traces | Traces | 490.27 | 1014.0 |
| Total | 100.0 | 100.0 | 1386.52 | 3578.9 |

6.D Hydrocodone/Acetaminophen ODTs:

A compression blend comprising taste-masked hydrocodone/acetaminophen microparticles from Example 6.B, above or taste-masked Hydrocodone/Acetaminophen microparticles from Example 6.C, above was combined with the rapidly dispersing microgranules from 1.E, above, and a pre-blend comprising microcrystalline cellulose, crospovidone, sucralose, and strawberry flavor, and compressed into Hydrocodone bitartrate/Acetaminophen ODTs, 10 mg/300 mg and 5 mg/500 mg (see Table 11 for compositions) using an Elizabeth Hata tablet press. While ODT lot# 1334-JMC-142 was compressed using magnesium stearate as an external lubricant, ODT lot# 1198-JMC-046 and 1198-JMC-062 were compressed using Sodium stearyl fumarate (PRUV®) as an internal lubricant. The tableting properties are listed in Table 12.

TABLE 11

Hydrocodone Bitartrate/Acetaminophen ODTs, 5 mg/500 mg & 10 mg/300 mg

| Item | Ingredient (mg/tablet) | Hydrocodone/Acetaminophen ODTs | | |
|---|---|---|---|---|
| | | 10 mg/300 mg 1334-JMC-142 mg/tablet | 10 mg/300 mg 1198-JMC-062 mg/tablet | 5 mg/500 mg 1198-046 mg/tablet |
| 1 | Sucralose/HPC/9% Hydrocodone/ Acetaminophen (from Example 6.B) | 123.11 | | |
| | Sucralose/HPC/5.7% Hydrocodone/ Acetaminophen (from Example 6.C) | | 184.50 | 92.25 |
| 2 | Acetaminophen Microcapsules (10%) | 225.88 | 172.33 | 476.35 |
| 3 | Rapidly Dispersing Granules | 542.01 | 443.97 | 454.10 |
| 4 | Microcrystalline Cellulose, NF | 110.00 | 110.00 | 140.00 |
| 5 | Mannitol, USP (Parteck ® M200) | | 110.00 | 140.00 |
| 6 | Crospovidone | 55.00 | | |
| | Croscarmellose Sodium (Ac-Di-Sol) | | 33.00 | 42.00 |
| 7 | Sucralose, NF | 13.75 | 18.70 | 23.80 |
| 8 | Artificial Cherry Flavor | 19.25 | 16.50 | 17.50 |
| 9 | Citric Acid | 11.00 | | |
| | Magnesium stearate (External) | Traces | | |
| | Sodium Stearyl Fumarate (PRUV) | | 11.00 | 14.00 |
| | Total | 1100.0 | 1100.0 | 1400.0 |

TABLE 12

Tableting Properties of Hydrocodone Bitartrate/Acetaminophen ODTs

| Lot# | Compression Force | Weight | Thickness | Hardness | Friability |
|---|---|---|---|---|---|
| ODTs 10-mg/300-mg | | | | | |
| 1334-142 | 13 kN | 1102 mg | 6.12 mm | 41.3 N | 0.51% |
| | 14 kN | 1101 mg | 6.03 mm | 46.4 N | 0.37% |
| 1198-062 | 12.5 kN | 1099 mg | 6.09 mm | 46.0 N | 0.20% |
| ODTs 5-mg/500-mg | | | | | |
| 1198-046 | 18 kN | 1402 mg | 6.11 mm | 53 N | 0.18% |
| | 20 kN | 1394 mg | 6.03 mm | 61 N | 0.05% |
| | 22 kN | 1390 mg | 5.97 mm | 67 N | 0.17% |

EXAMPLE 7

7.A Microencapsulation of Acetaminophen (PE420):

A 200-gallon solvent coacervation system was charged with acetaminophen (94.1 kg of A137 (Semi-fine grade)), Ethylcellulose (10.5 kg of Ethocel Premium 100), Epolene (phase inducer, 2.1 kg) and cyclohexane (142 gallons) while agitating at 60±5 RPM. Acetaminophen was taste-masked by solvent coacervation. A computer controlled "heat to 80° C.- and hold" cycle with the agitation speed set at 107±5 RPM was used to achieve a temperature of 80° C. to dissolve the ethylcellulose in the coacervation system. Thereafter the system was subjected to a cooling cycle to <28° in not less than 45 min to encapsulate the acetaminophen crystals with a smooth coating at 10% by weight, and avoiding the formation of agglomerates. The microcapsules were vacuum-filtered, washed with cyclohexane, and dried in a fluid bed dryer using a 3-step temperature (e.g., 25° C., 35° C., 99° C.) for 4 to 6 hrs to achieve a residual cyclohexane level of less than 1000 ppm. The microcapsules were sieved through a US 35 mesh sieve. Following the same procedure, several batches of microcapsules (batch size: 105 kg) were prepared at a coating weight of 10% in the 200 gallon system.

7.B Taste-Masked Hydrocodone/Acetaminophen Microparticles (PE408)

Hydrocodone bitartrate (3.6 kg) was slowly added to 36 kg of purified water and stirred until dissolved, followed by 0.4 kg Klucel LF, which was stirred until dissolved. Acetaminophen microcapsules (6% EC-100 coating; 56.0 kg) from Example 6.A, above were coated with hydrocodone by spraying the drug-layering formulation (10% solids) in a Fluid Air FA0300 equipped with an 18" bottom spray Wurster insert, 50 mm partition gap, 200 mesh product retention screen, 3.0 mm nozzle tip diameter at the following processing conditions—product temperature: 33±3° C.; inlet air volume: 500 CFM; spray rate: 16-26% ramp-up; atomization pressure 30 psi) for a hydrocodone bitartrate load of 6.0%. A protective sealant coating solution of hydroxypropylcellulose (3.2 kg dissolved) and sodium stearyl fumarate (0.5 kg suspended) in 110.9 kg acetone/12.3 kg water) was sprayed onto the drug-layered particles for a coating weight of 5%, followed by a taste-masking coating with sucralose (3.3 kg) dissolved in 59.4 kg acetone/6.6 kg water using the following process conditions: Inlet temperature: 53±2° C.; product temperature: 37±2° C.; spray rate: 19-25% ramp-up; inlet air volume: 500 CFM, dried for 5 minutes to reduce residual moisture and sieved through 30 and 80 mesh sieves to discard over sized particles and fines.

7.C Hydrocoden Bitartrate/Acetaminophen ODTs 5-mg/500-mg

Compression blend PF427 (Hydrocodone/Acetaminophen 5 mg/500 mg) comprising taste-masked acetaminophen microparticles (50.81 kg of PE420 from Ex. 7.A, above), taste-masked Hydrocodone/Acetaminophen microparticles (9.98 kg of PE408 from Ex. 7.B, above), rapidly dispersing microgranules (50.41 kg from Ex 1.E and spray dried mannitol (15 kg Parteck M200), and other excipients (pre-blend consisting of microcrystalline cellulose (15 kg of Avicel PH101, Croscarmellose sodium (1.5 kg Ac-Di-Sol), Sucralose (2.55 kg), was prepared by blending the ingredients in a 10 cu-ft V-blender (batch size: 150 kg) for 20 min followed by the addition of sodium stearyl fumarate (1.5 kg) and blending for 5 minutes. This compression blend was compressed into Hydrocodone bitartrate/Acetaminophen ODTs, 5 mg/500 mg using an Elizabeth Hata tablet press—Matsui's ExLub system under the tableting conditions listed in Table 13. Following a similar procedure, compression blend PF428 comprising taste-masked acetaminophen microparticles (23.29 kg of PE420 from Ex. 7.A, above), taste-masked Hydrocodone/Acetaminophen microparticles (25.39 kg of PE408 from Ex. 7.B, above), rapidly dispersing microgranules (63.52 kg from Ex 1.E and spray dried mannitol (15 kg Parteck M200), pre-blend consisting of microcrystalline cellulose (15 kg of Avicel PH101, Croscarmellose sodium (1.5 kg Ac-Di-Sol), Sucralose (2.55 kg), and sodium stearyl fumarate (1.5 kg), was prepared and compressed into Hydrocodone bitartrate/Acetaminophen ODTs, 5 mg/500 mg (see Table 13 for parameters).

TABLE 13

Tableting Parameters for PF427 and PF428

| Product | Hydrocodone/Acetaminophen ODTs | |
|---|---|---|
| Strength; Lot# | 5 mg/500 mg; PF427* | 10 mg/300 mg; PF428** |
| Tableting Parameter | | |
| Turn Table Speed (RPM) | 25 | 25 |
| Main Compression Force | 24 kN | 20 kN |
| Pre. Compression 4.3 kN Force | 5.0 kN | 4.3 kN |
| Force Feeder | 90% | 90% |
| Tablet Weight (mg) | 1400 | 1100 |
| Tablet Hardness (N) | 75 | 70 |
| Friability (%) | NMT 0.4% | NMT 0.4% |

*17 mm, Flat face radius edge with a logo on one side and 5/500 on the other
**15 mm, Flat Face Radius Edge with a logo on one side and 10/300 on the other

EXAMPLE 8

8.A Acetaminophen Microparticles by Controlled Spheronization

Povidone (PVP K-30; 50 g) is slowly added to purified water (500 g) with constant stirring to prepare a polymer binder solution at 10% w/w solids. Acetaminophen powder from Covidien (2000 g) is blended with 10 g of colloidal silica (a flow aid, Cab-O-Sil M-5P from Cabot Corporation) and povidone (50 g) in a V-blender and charged into the product bowl of Granurex GX-35 from Vector Corporation (Iowa, USA). The 10% PVP binder solution is sprayed into the rotating material bed at a controlled rate. Optimized process parameters during pellet formation—process air temperature: ~19-20° C.; product temperature: 16±2° C.; rotor speed: 425 RPM; external air supply: 150 L/min; spray rate: 15 RPM (~8 mL/min); pressure drop across slit: 1.3-11 mm in water. Optimized process parameters during drying of pellets—process air volume: 30 CFM; process air temperature: ~60° C.; product temperature: 35° C. (to stop drying); rotor speed: 180 RPM; slit air volume: 10 CFM; processing time: 40 min. About 65% of the pellets thus prepared have a size in the range of 40-80 mesh.

8.B SR Coated Acetaminophen Microparticles

OPADRY® Clear (30.6 g) is added to purified water while stirring to dissolve. A Glatt GPCG 3 equipped with a 6" bottom spray Wurster 8" high column, partition column gap of 15 mm from the 'B' bottom air distribution plate covered with a 200 mesh product retention screen (1.0 mm port nozzle) is charged with acetaminophen microparticles (1500 g) from Example 8.A, above and coated with the protective sealant coating solution (10 wt. % solids) at 4 mL/min, ramping up to about 8 mL/min. Process conditions—product temperature: 38-42° C.; process air volume: about 150 CFM. Ethylcellulose (153 g Ethocel Standard 10 Premium) is slowly added to acetone (2185 g) in a stainless steel container to dissolve while constantly stirring. Then purified water (244 g) is added to the ethylcellulose solution with continued stirring, followed by the addition of the plasticizer, i.e., triethyl citrate (17 g) to dissolve. Seal-coated acetaminophen microparticles are spray coated in the same unit with this solution for a 10% weight gain. Samples are pulled at a coating of 5.0 and 7.5% by weight for drug release testing. The dried particles are sieved using 30 and 60 mesh sieves to discard agglomerates/fines. A 2% seal coat with Klucel LF is also applied to avoid potential interaction between the polymer/plasticizer and low-dose drug (e.g., hydrocodone).

8.C Hydrocodone Bitartrate Coated Acetaminophen Microparticles:

Hydrocodone bitartrate is layered onto seal-coated SR microcapsules from Example 8.B, above in the Glatt GPCG 3 for a weight gain of 4% as described in Example 1.C, above. Following the drug layering, a seal coating of Klucel LF at 5% by weight is sprayed onto the hydrocodone-layered particles, followed by a taste-masking coating of sucralose at 5% weight gain as disclosed in the earlier examples. Following the coating, the microparticles are dried for 5 minutes to reduce residual moisture and sieved through 30 and 60 mesh sieves to discard oversized particles and fines 8.D Hydrocodone/Acetaminophen SR ODT:

Hydrocodone/Acetaminophen SR microparticles from Example 8.C, above, rapidly dispersing microgranules from Example 1.E, above and a pre-blend comprising microcrystalline cellulose, sucralose, strawberry flavor, and crospovidone are blended together in a V-blender and compressed into Hydrocodone/Acetaminophen SR ODTs, 2.5-mg/325 mg, 5 mg/500 mg, and 10 mg/300 mg using an Elizabeth Hata tablet press equipped with a Matsui Ex-Lub lubricating system that uses magnesium stearate as an external lubricant to lubricate punch and die surfaces prior to compression.

These examples demonstrate that the ODT formulations comprising microparticles comprising high-dose sustained release acetaminophen/low-dose taste-masked hydrocodone exhibit acceptable tableting properties (e.g., hardness, friability, uniformity of dosage forms, low in vitro/in vivo disintegration time, rapid dissolution of hydrocodone, 9-12 hr sustained-release profile for acetaminophen and acceptable organoleptic properties which significantly improve patient-compliance.

Changes may be made by persons skilled in the art in the construction and the various components and assembly described herein or in the steps or the sequence of steps of the method of manufacture described therein without departing from the spirit and scope of the invention as described herein.

The invention claimed is:
1. A pharmaceutical composition comprising a first population of non-opioid analgesic/opioid analgesic drug-containing microparticles, wherein the drug-containing microparticles comprise:
    (a) a first core comprising a non-opioid analgesic drug;
    (b) a first coating disposed over the first core, comprising an opioid analgesic drug; and
    (c) a second coating disposed over the first core, comprising a water-insoluble polymer; and further comprising a second population of non-opioid analgesic drug-containing particles, wherein the second population of non-opioid analgesic drug-containing particles comprise:
    (i) a second core comprising the non-opioid analgesic drug; and
    (ii) a third coating comprising a water-insoluble polymer disposed over the second core, wherein the water-insoluble polymer of the third coating is the same as or different from the water-insoluble polymer of the second coating.

2. The pharmaceutical composition of claim 1, wherein the weight ratio of non-opioid analgesic drug to opioid analgesic drug in the first population of non-opioid analgesic/opioid analgesic drug-containing microparticles is at least about 20:1.

3. The pharmaceutical composition of claim 1, wherein the non-opioid analgesic drug-containing core of the first population of non-opioid analgesic/opioid analgesic drug-containing microparticles comprises particles of the non-opioid analgesic drug.

4. The pharmaceutical composition of claim 1, wherein the second coating further comprises a plasticizer.

5. The pharmaceutical composition of claim 4, wherein the plasticizer is free of phthalates.

6. The pharmaceutical composition of claim 4, wherein the plasticizer is selected from the group consisting of glycerol, glycerol esters, acetylated mono- or diglycerides, glyceryl monostearate, glyceryl triacetate, glyceryl tributyrate, phthalates, dibutyl phthalate, diethyl phthalate, dimethyl phthalate, dioctyl phthalate, citrates, acetylcitric acid tributyl ester, acetylcitric acid triethyl ester, tributyl citrate, acetyltributyl citrate, triethyl citrate, glyceroltributyrate, sebacates, diethyl sebacate, dibutyl sebacate, adipates, azelates, benzoates, chlorobutanol, polyethylene glycols, vegetable oils, fumarates, diethyl fumarate, malates, diethyl malate, oxalates, diethyl oxalate, succinates, dibutyl succinate, butyrates, cetyl alcohol esters, malonates, diethyl malonate, castor oil, and combinations thereof.

7. The pharmaceutical composition of claim 1, wherein the second coating substantially masks the taste of the non-opioid analgesic and/or the opioid analgesic.

8. The pharmaceutical composition of claim 7, wherein the second coating further comprises a gastrosoluble polymer or a gastrosoluble pore-former.

9. The pharmaceutical composition of claim 8, wherein the water-insoluble polymer of the first population of non-opioid analgesic/opioid analgesic drug-containing microparticles is selected from the group consisting of water-insoluble cellulose ethers, ethylcellulose, water-insoluble cellulose esters, cellulose acetate, cellulose triacetate, cellulose acetate butyrate, polyvinyl acetate, neutral methacrylic acid-methylmethacrylate copolymers, and mixtures thereof; and the gastrosoluble pore-former is selected from the group consisting of maltrin, aminoalkyl methacrylate copolymers, polyvinylacetal diethylaminoacetate, calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium phosphate, and mixtures thereof.

10. The pharmaceutical composition of claim 1, wherein the water-insoluble polymer of the first population of non-opioid analgesic/opioid analgesic drug-containing microparticles is selected from the group consisting of water-insoluble cellulose ethers, ethylcellulose, water-insoluble cellulose esters, cellulose acetate, cellulose triacetate, cellulose acetate butyrate, polyvinyl acetate, neutral methacrylic acid-methylmethacrylate copolymers, and mixtures thereof.

11. The pharmaceutical composition of claim 1, wherein the second coating is disposed between the core and the first coating of the first population of non-opioid analgesic/opioid analgesic drug-containing microparticles.

12. The pharmaceutical composition of claim 11, further comprising a fourth coating disposed over the first coating, wherein the fourth coating comprises a water-insoluble polymer which is the same as or different from the water-insoluble polymer of the second coating.

13. The pharmaceutical composition of claim 12, wherein the fourth coating substantially masks the taste of the opioid analgesic.

14. The pharmaceutical composition of claim 1, further comprising a fifth coating disposed between the core and the first coating of the first population of non-opioid analgesic/opioid analgesic drug-containing microparticles, wherein the fifth coating comprises a water-insoluble polymer which is the same as or different from the water-insoluble polymer of the second coating.

15. The pharmaceutical composition of claim 14, wherein the fifth coating substantially masks the taste of the non-opioid analgesic.

16. The pharmaceutical composition of claim 15, wherein the fifth coating further comprises a gastrosoluble polymer or a gastrosoluble pore-former.

17. The pharmaceutical composition of claim 1, further comprising a flavorant coating disposed over the first coating, wherein the flavorant coating comprises a sweetener.

18. The pharmaceutical composition of claim 17, wherein the sweetener is selected from the group consisting of sucralose, lactitol, maltitol, sorbitol, and combinations thereof.

19. The pharmaceutical composition of claim 17, wherein the second coating is disposed between the core and the first coating.

20. The pharmaceutical composition of claim 19, wherein the second coating substantially modifies the release of the non-opioid analgesic.

21. The pharmaceutical composition of claim 1, wherein the second coating is disposed between the core and the first coating, and the second coating substantially modifies the release of the non-opioid analgesic.

22. The pharmaceutical composition of claim 21, wherein a fourth coating disposed over the first coating comprises a flavorant coating comprising a sweetener; and the fourth coating substantially masks the taste of the opioid analgesic.

23. The pharmaceutical composition of claim 1, wherein the non-opioid analgesic is a non-steroidal anti-inflammatory drug and the opioid analgesic is an opioid analgesic drug.

24. The pharmaceutical composition of claim 23, wherein the non-opioid analgesic is selected from the group consisting of acetaminophen, aspirin, ibuprofen, ketoprofen, meloxicam, diclofenac potassium, etodolac, sulindac, indomethacin, and celecoxib; and the opioid analgesic is selected from the group consisting of hydrocodone, oxymorphone, buprenorphine, fentanyl, and hydromorphone.

25. The pharmaceutical composition of claim 24, wherein the non-opioid analgesic comprises acetaminophen, and the opioid analgesic comprises hydrocodone.

26. The pharmaceutical composition of claim 25, further comprising a flavorant coating comprising a sweetener disposed over the first coating, wherein the second coating is disposed between the core and the first coating.

27. The pharmaceutical composition of claim 26, wherein the second coating comprises ethylcellulose, and further comprising a fourth coating over the first coating comprising sucralose and an optional binder.

28. A dosage form comprising the composition of claim 1 and one or more pharmaceutically acceptable excipients.

29. A dosage form comprising the composition of claim 23 and one or more pharmaceutically acceptable excipients.

30. The dosage form of any one of claim 28 or 29, wherein the dosage form further comprises rapidly dispersing granules comprising a disintegrant and a sugar alcohol and/or saccharide; wherein the dosage form is an orally disintegrating tablet (ODT).

31. The dosage form of claim 30, wherein the ODT substantially disintegrates within about 30 seconds when tested according to the USP <701>Disintegration Test.

32. The dosage form of claim 30, wherein the ODT releases at least about 75% of the total amount of the non-opioid analgesic and at least about 75% of the opioid analgesic in 30 minutes, when dissolution tested using USP Apparatus 1 (Baskets @ 100 rpm) or Apparatus 2 (Paddles @ 50 rpm), in 900 mL of a pH 1.2 buffer.

33. The dosage form of claim 30 in the form of an ODT, comprising 500 mg of acetaminophen and 5 mg of hydrocodone bitartrate, wherein the ODT has an acetaminophen $C_{max}$ of 80-125% of 6115 ng/mL, a hydrocodone bitartrate $C_{max}$ of 80-125% of 20.14 ng/mL, an acetaminophen AUC of 80-125% of 19920 ng·hr/mL, and a hydrocodone bitartrate AUC of 80-125% of 141 ng·hr/mL.

34. The dosage form of claim 30 in the form of an ODT, comprising 300 mg of acetaminophen and 10 mg of hydrocodone bitartrate, wherein the ODT has an acetaminophen $C_{max}$ of 80-125% of 3915 ng/mL, a hydrocodone bitartrate $C_{max}$ of 80-125% of 40.53 ng/mL, an acetaminophen AUC of 80-125% of 12794 ng·hr/mL, and a hydrocodone bitartrate AUC of 80-125% of 280 ng·hr/mL.

35. The dosage form of claim 30, wherein said the disintegrant is selected from the group consisting of crospovidone, sodium starch glycolate, crosslinked carboxymethyl cellulose of sodium, low-substituted hydroxypropylcellulose and mixtures thereof and the sugar alcohol or saccharide is selected from the group consisting of mannitol, xylitol, maltol, maltitol, sorbitol, lactose, sucralose, maltose, and combinations thereof.

36. A method for preparing the pharmaceutical composition of claim 1, comprising:
 (1) preparing cores comprising a non-opioid analgesic drug;
 (2) applying a first coating over the non-opioid analgesic drug-containing cores of step (1), wherein said first coating comprises an opioid analgesic drug, thereby forming non-opioid analgesic/opioid analgesic drug-containing microparticles;
 (3) applying a second coating comprising a water-insoluble polymer, wherein said second coating is applied either before or after step (2), thereby forming a first population of non-opioid analgesic/opioid analgesic drug containing microparticles; and
 (4) admixing the product of step (3) with a second population of non-opioid analgesic drug-containing particles.

37. A method of treating pain comprising administering a therapeutically effective amount of the pharmaceutical composition of claim 24 to a patient in need thereof.

38. The method of claim 36, further comprising one or more of the following:

(5) coating the non-opioid analgesic/opioid analgesic drug-containing microparticles with a flavorant coating;

(6) blending the admixture of step (4) with rapidly dispersing microgranules and optionally one or more excipients into a homogeneous blend; and (7) compressing the blend to form a uniform ODT;
wherein a blend of homogeneity of step (6) meets United States Phamacopoeia requirements.

39. The method of claim 38, wherein the flavorant coating comprises a sweetner.

40. The method of claim 39, wherein the sweetner is selected from the group consisting of sucralose, lactitol, maltitol, sorbitol, and combinations thereof.

41. The pharmaceutical composition of claim 1, wherein the weight ratio of non-opioid analgesic drug to opioid analgesic drug in the first population of non-opioid analgesic/opioid analgesic drug-containing microparticles is at about 20:1 to about 100:1.

42. The method of claim 36, wherein the second coating is applied before step (2).

43. The method of claim 36, wherein the second coating is applied after step (2).

44. The method of claim 42, wherein a third coating comprising a water-insoluble polymer is applied after step (2).

* * * * *